「12」 United States Patent
Wing et al.

(10) Patent No.: US 6,989,003 B2
(45) Date of Patent: Jan. 24, 2006

(54) OBTURATOR AND CANNULA FOR A TROCAR ADAPTED FOR EASE OF INSERTION AND REMOVAL

(75) Inventors: Daniel M. Wing, Utica, NY (US); Stephen J. Scheuermann, Oneida, NY (US); Deborah A. Laun, Syracuse, NY (US)

(73) Assignee: ConMed Corporation, Utica, NY (US)

( * ) Notice: Subject to any disclaimer, the term of this patent is extended or adjusted under 35 U.S.C. 154(b) by 0 days.

(21) Appl. No.: 09/944,190

(22) Filed: Aug. 31, 2001

(65) Prior Publication Data

US 2003/0045834 A1 Mar. 6, 2003

(51) Int. Cl.
*A61M 5/178* (2006.01)

(52) U.S. Cl. .................. 604/161; 604/164.04; 606/185
(58) Field of Classification Search ............ 604/164.07, 604/164.01, 164.11, 68.04, 167.01, 167.02, 604/165.01–165.04, 166.01, 164.09, 164.04, 604/161, 506; 606/167, 181, 184, 185
See application file for complete search history.

(56) References Cited

U.S. PATENT DOCUMENTS

| | | | |
|---|---|---|---|
| 1,045,906 A | 12/1912 | Sweet | |
| 1,365,167 A | 1/1921 | Gates | |
| 2,069,075 A | 1/1937 | Lunn | 215/38 |
| 3,039,468 A | 6/1962 | Price | 128/347 |

(Continued)

FOREIGN PATENT DOCUMENTS

| | | |
|---|---|---|
| EP | 0150281 A1 | 8/1985 |
| EP | 0535974 A1 | 4/1993 |
| EP | 0 792 660 A3 | 2/1997 |
| WO | WO 00/45720 | 4/2000 |

OTHER PUBLICATIONS

Laun, pending U.S. Appl. No. 29/168,574, filed Oct. 4, 2002, entitled TROCAR.
Laun, pending U.S. Appl. No. 29/180,624, filed Apr. 28, 2003, entitled "OBTURATOR,".
Laun, pending U.S. Appl. No. 29/180,774, filed Apr. 28, 2003, entitled "Cannula Head,".
Witkowski, U.S. Appl. No. 29/180,667, filed Apr. 28, 2003, entitled "Cannula Tube,".
ConMed Brochure entitled "TroGard Finesse", dated Feb. 2000.
ConMed Brochure entitled "Advanced Patient Benefits, Single–Use Trocars", dated 2000.
ConMed brochure entitled, "Unsurpassed Control, Resposable Trocars," dated 1997.

*Primary Examiner*—Nicholas D. Lucchesi
*Assistant Examiner*—Matthew F DeSanto
(74) *Attorney, Agent, or Firm*—John Pietrangelo; Heslin Rothenberg Farley & Mesiti, P.C.

(57) ABSTRACT

A surgical trocar device having an obturator and cannula that requires less force to insert and remove from tissue. The cannula includes a head assembly and the obturator includes a cap assembly that have cooperating surfaces that bear against each other so that when the obturator is rotated about its axis the obturator is axially deflected within the cannula and thus more easily removed from the tissue into which the obturator is inserted. The tip of the obturator and the end of the cannula are designed to minimize tissue damage and insertion effort by providing a smooth, unencumbered surface transition. In one aspect of the invention, the tip of the cannula is smooth, continuous, and flexible and can radially deflect when the larger-diameter obturator is inserted or withdrawn though the cannula. In another aspect, the axial deflection of the obturator and the flexible head of the cannula work in concert and the obturator can be axially deflected and removed from the cannula and the tissue into which the obturator is inserted by a simple twisting of the obturator. Another aspect of the invention is a cannula having a resilient sealing element that minimizes the escape of fluid during insertion or removal of an obturator.

13 Claims, 14 Drawing Sheets

U.S. PATENT DOCUMENTS

| | | | |
|---|---|---|---|
| 3,716,163 A | 2/1973 | Marcel | 215/47 |
| 3,789,852 A | 2/1974 | Kim et al. | 128/347 |
| 3,945,525 A | 3/1976 | Jones | 215/232 |
| 4,171,057 A | 10/1979 | Gach | 215/211 |
| 4,405,307 A * | 9/1983 | Taylor | 604/165.01 |
| 4,424,833 A | 1/1984 | Spector et al. | 137/849 |
| 4,464,169 A | 8/1984 | Semm | 604/26 |
| 4,490,136 A | 12/1984 | Ekbladh et al. | 604/22 |
| 4,535,773 A | 8/1985 | Yoon | 604/51 |
| 4,576,589 A | 3/1986 | Kraus et al. | 604/8 |
| 4,588,398 A | 5/1986 | Daugherty et al. | 604/265 |
| 4,601,710 A | 7/1986 | Moll | 604/165 |
| 4,654,030 A | 3/1987 | Moll et al. | 604/165 |
| 4,676,774 A | 6/1987 | Semm et al. | 604/26 |
| 4,809,679 A | 3/1989 | Shimonaka et al. | 128/4 |
| 4,846,791 A | 7/1989 | Hattler et al. | 604/43 |
| 4,874,362 A | 10/1989 | Wiest et al. | 604/26 |
| 4,902,280 A | 2/1990 | Lander | 604/165 |
| 4,909,798 A | 3/1990 | Fleischhacker et al. | 604/256 |
| 4,931,042 A | 6/1990 | Holmes et al. | 604/164 |
| 4,943,280 A | 7/1990 | Lander | 604/169 |
| 4,966,578 A | 10/1990 | Baier et al. | 604/26 |
| 4,994,027 A | 2/1991 | Farrell | 604/53 |
| 5,009,643 A | 4/1991 | Reich et al. | 604/165 |
| 5,030,206 A | 7/1991 | Lander | 604/164 |
| 5,053,016 A | 10/1991 | Lander | 604/169 |
| 5,057,082 A | 10/1991 | Burchette, Jr. | 604/164 |
| 5,066,288 A | 11/1991 | Deniega et al. | 604/274 |
| 5,073,169 A | 12/1991 | Raiken | 604/180 |
| 5,104,382 A | 4/1992 | Brinkerhoff et al. | 604/165 |
| 5,104,383 A | 4/1992 | Shichman | 604/167 |
| 5,112,321 A | 5/1992 | Hiltebrandt | 604/264 |
| 5,114,407 A | 5/1992 | Burbank | 604/164 |
| 5,122,122 A | 6/1992 | Allgood | 604/174 |
| 5,129,885 A | 7/1992 | Green et al. | 604/164 |
| 5,137,509 A | 8/1992 | Freitas | 604/26 |
| 5,147,316 A | 9/1992 | Castillenti | 604/164 |
| 5,152,754 A | 10/1992 | Plyley et al. | 604/164 |
| 5,154,701 A | 10/1992 | Cheer et al. | 604/167 |
| 5,158,552 A | 10/1992 | Borgia et al. | 604/165 |
| 5,203,769 A | 4/1993 | Clement et al. | 604/32 |
| 5,209,736 A | 5/1993 | Stephens et al. | 604/164 |
| 5,217,451 A | 6/1993 | Freitas | 606/1 |
| 5,224,929 A | 7/1993 | Remiszewski | 604/30 |
| 5,224,954 A | 7/1993 | Watts et al. | 606/205 |
| 5,261,891 A | 11/1993 | Brinkerhoff et al. | 604/165 |
| 5,263,937 A * | 11/1993 | Shipp | 604/166.01 |
| 5,279,575 A | 1/1994 | Sugarbaker | 604/174 |
| 5,290,294 A * | 3/1994 | Cox et al. | 606/108 |
| 5,300,070 A | 4/1994 | Gentelia et al. | 606/45 |
| 5,320,611 A | 6/1994 | Bonutti et al. | 604/264 |
| 5,342,383 A | 8/1994 | Thomas | 606/190 |
| 5,346,459 A | 9/1994 | Allen | 606/185 |
| 5,350,393 A | 9/1994 | Yoon | 606/185 |
| 5,357,974 A | 10/1994 | Baldridge | 128/754 |
| 5,368,046 A | 11/1994 | Scarfone et al. | 128/754 |
| 5,372,588 A | 12/1994 | Farley et al. | 604/164 |
| 5,380,288 A | 1/1995 | Hart et al. | 604/167 |
| 5,385,553 A | 1/1995 | Hart et al. | 604/167 |
| 5,389,077 A | 2/1995 | Melinyshyn et al. | 604/117 |
| 5,409,462 A | 4/1995 | Ross | 604/166 |
| D358,209 S | 5/1995 | Petruschke et al. | D24/146 |
| 5,423,760 A | 6/1995 | Yoon | 604/165 |
| 5,431,676 A | 7/1995 | Dubrul et al. | 606/185 |
| 5,449,370 A | 9/1995 | Vaitekunas | 606/169 |
| 5,549,565 A | 8/1996 | Ryan et al. | 604/167 |
| 5,556,411 A | 9/1996 | Taoda et al. | 606/185 |
| 5,562,677 A | 10/1996 | Hildwein et al. | 606/108 |
| 5,575,804 A | 11/1996 | Yoon | 606/185 |
| 5,580,344 A | 12/1996 | Hasson | 600/219 |
| 5,603,702 A | 2/1997 | Smith et al. | 604/256 |
| 5,697,913 A | 12/1997 | Sierocuk et al. | 604/164 |
| 5,709,671 A | 1/1998 | Stephens et al. | 604/264 |
| 5,735,867 A | 4/1998 | Golser et al. | 606/185 |
| 5,800,451 A | 9/1998 | Buess et al. | 606/185 |
| 5,807,338 A * | 9/1998 | Smith et al. | 604/164.01 |
| 5,817,061 A | 10/1998 | Goodwin et al. | 604/164 |
| 5,824,002 A | 10/1998 | Gentelia et al. | 604/164 |
| 5,827,228 A | 10/1998 | Rowe | 604/167 |
| 5,851,216 A | 12/1998 | Allen | 606/185 |
| 5,857,982 A | 1/1999 | Milliman et al. | 600/567 |
| 5,865,807 A | 2/1999 | Blake, III | 604/167 |
| 5,868,714 A | 2/1999 | Danks | 604/256 |
| 5,879,332 A | 3/1999 | Schwemberger et al. | 604/164 |
| 5,897,503 A | 4/1999 | Lyon et al. | 600/459 |
| 5,904,699 A | 5/1999 | Schwemberger et al. | 606/185 |
| 5,916,232 A | 6/1999 | Hart | 606/185 |
| 5,941,852 A * | 8/1999 | Dunlap et al. | 604/164.11 |
| 5,944,208 A | 8/1999 | Gale | 215/296 |
| 5,971,960 A * | 10/1999 | Flom et al. | 604/174 |
| 5,984,941 A | 11/1999 | Wilson et al. | 606/185 |
| 5,989,224 A | 11/1999 | Exline et al. | 604/167 |
| 5,989,228 A | 11/1999 | Danks et al. | 604/256 |
| 5,993,471 A * | 11/1999 | Riza et al. | 606/185 |
| 5,997,510 A * | 12/1999 | Schwemberger | 604/164.11 |
| D426,635 S | 6/2000 | Haberland et al. | D24/146 |
| 6,142,981 A | 11/2000 | Heck et al. | 604/256 |
| 6,159,182 A | 12/2000 | Davis et al. | 604/167.06 |
| 6,162,236 A | 12/2000 | Osada | 606/185 |
| 6,497,687 B1 | 12/2002 | Blanco | 604/274 |
| 2003/0060770 A1 | 3/2003 | Wing et al. | 604/164.07 |
| 2003/0109894 A1 | 6/2003 | Blanco | 606/167 |

* cited by examiner

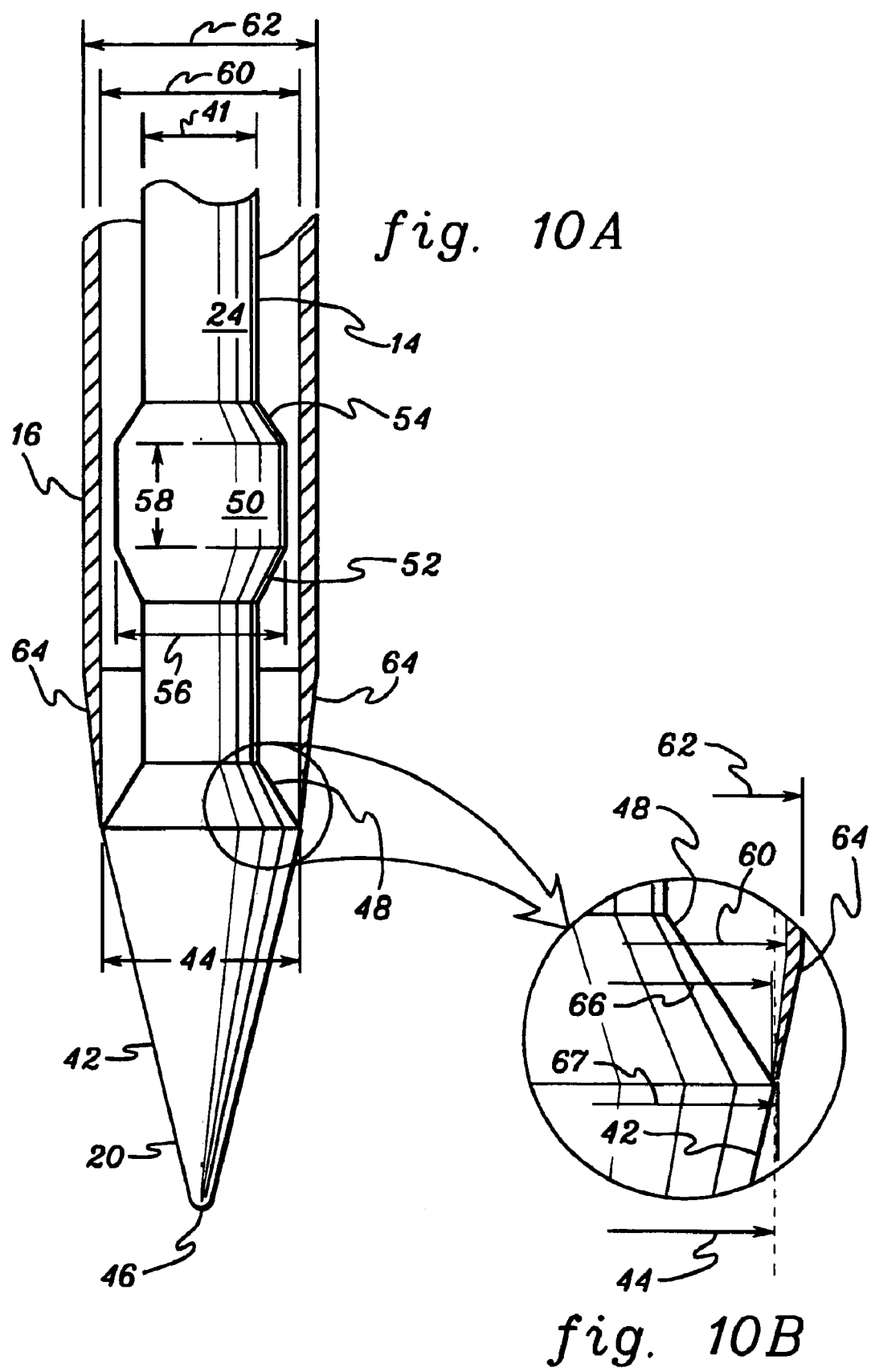

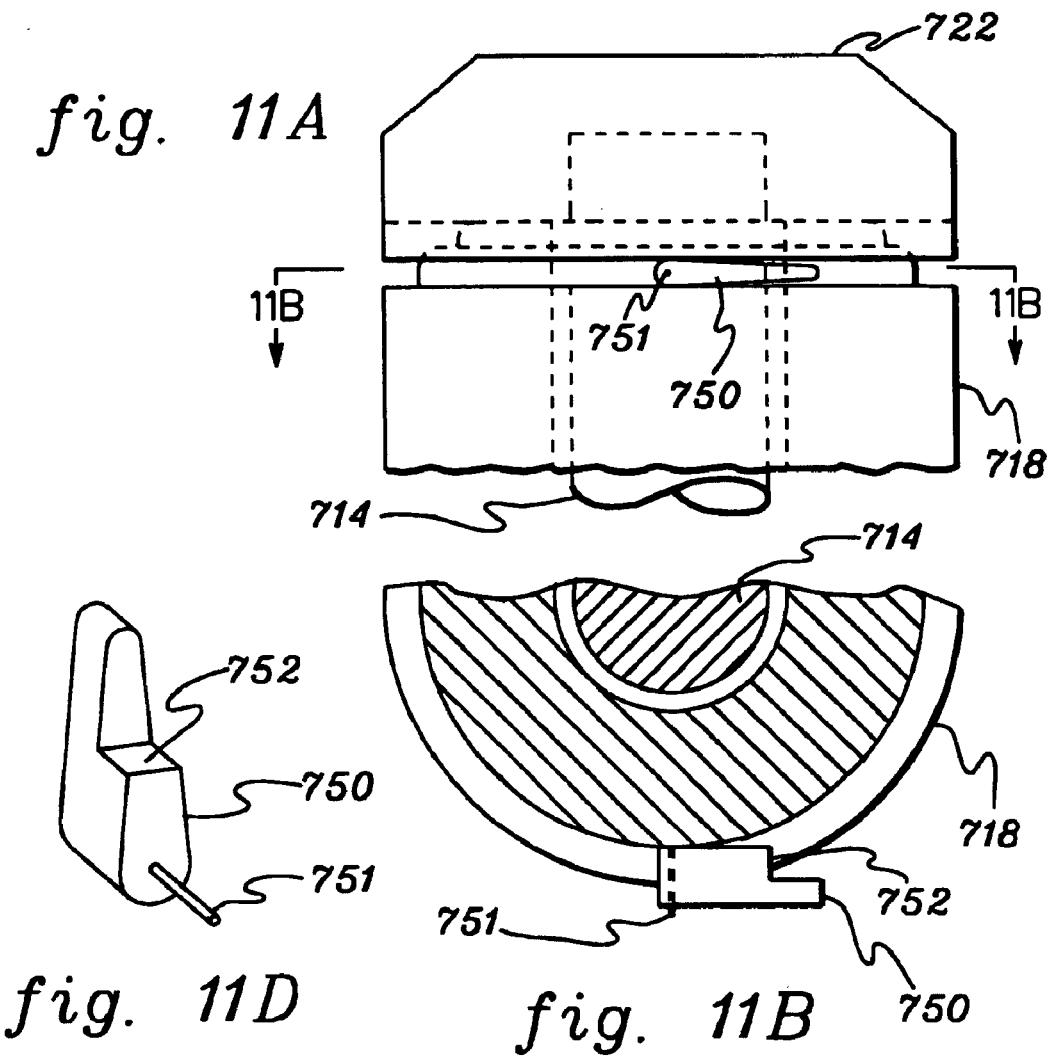
fig. 11A
fig. 11D    fig. 11B
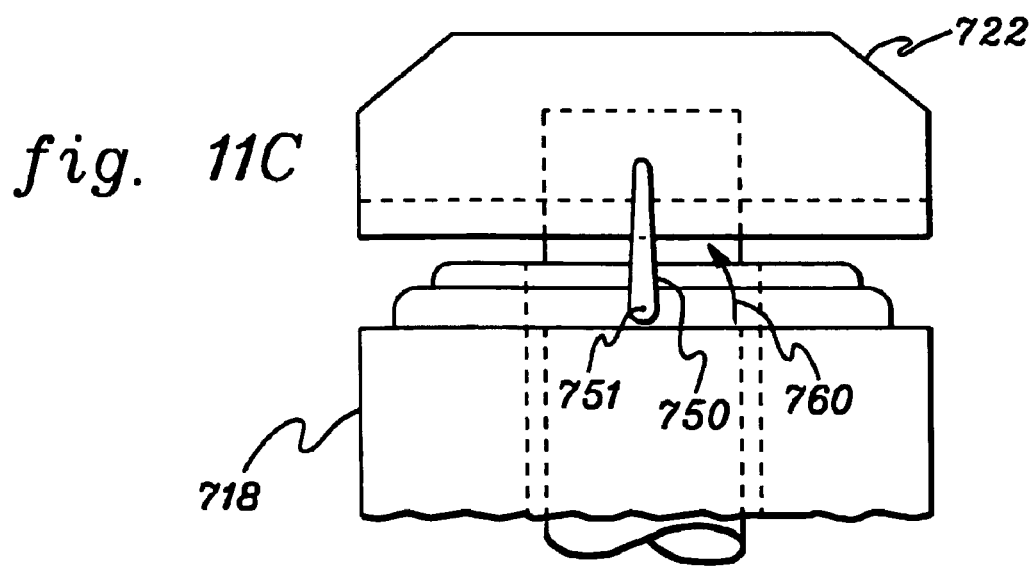
fig. 11C

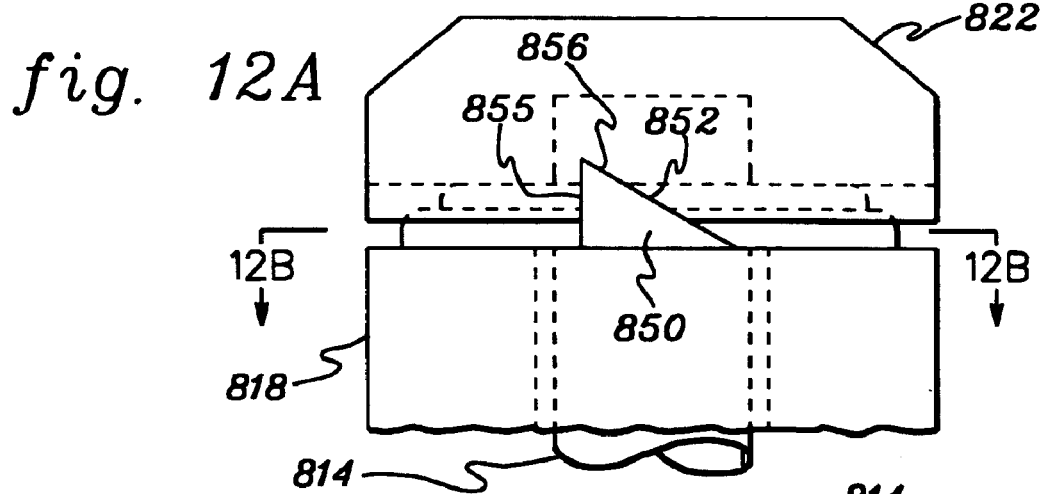
fig. 12A
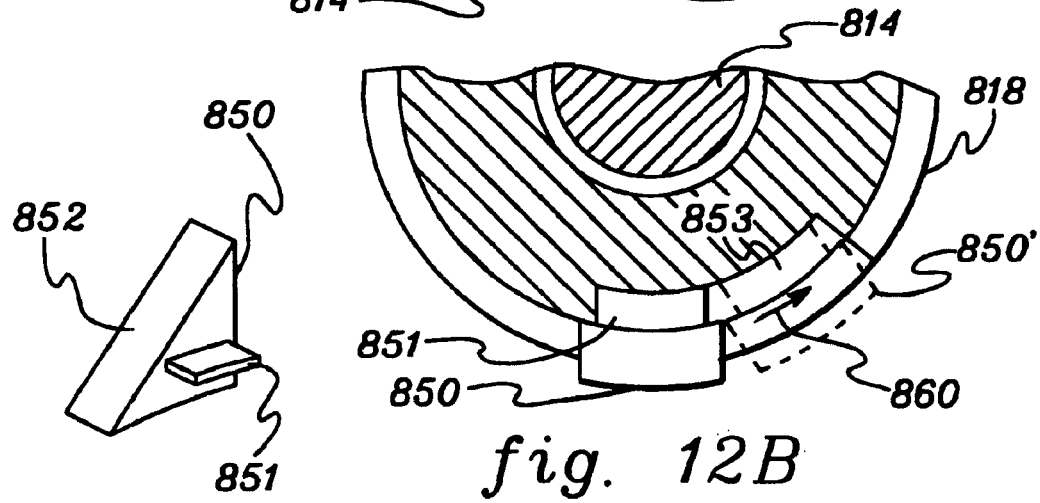
fig. 12D
fig. 12B
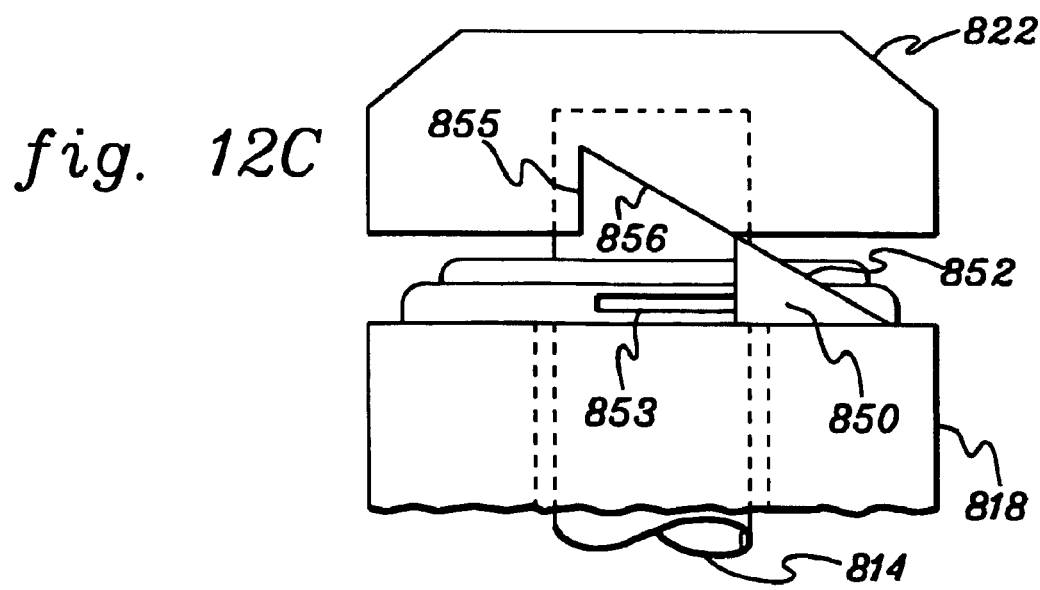
fig. 12C

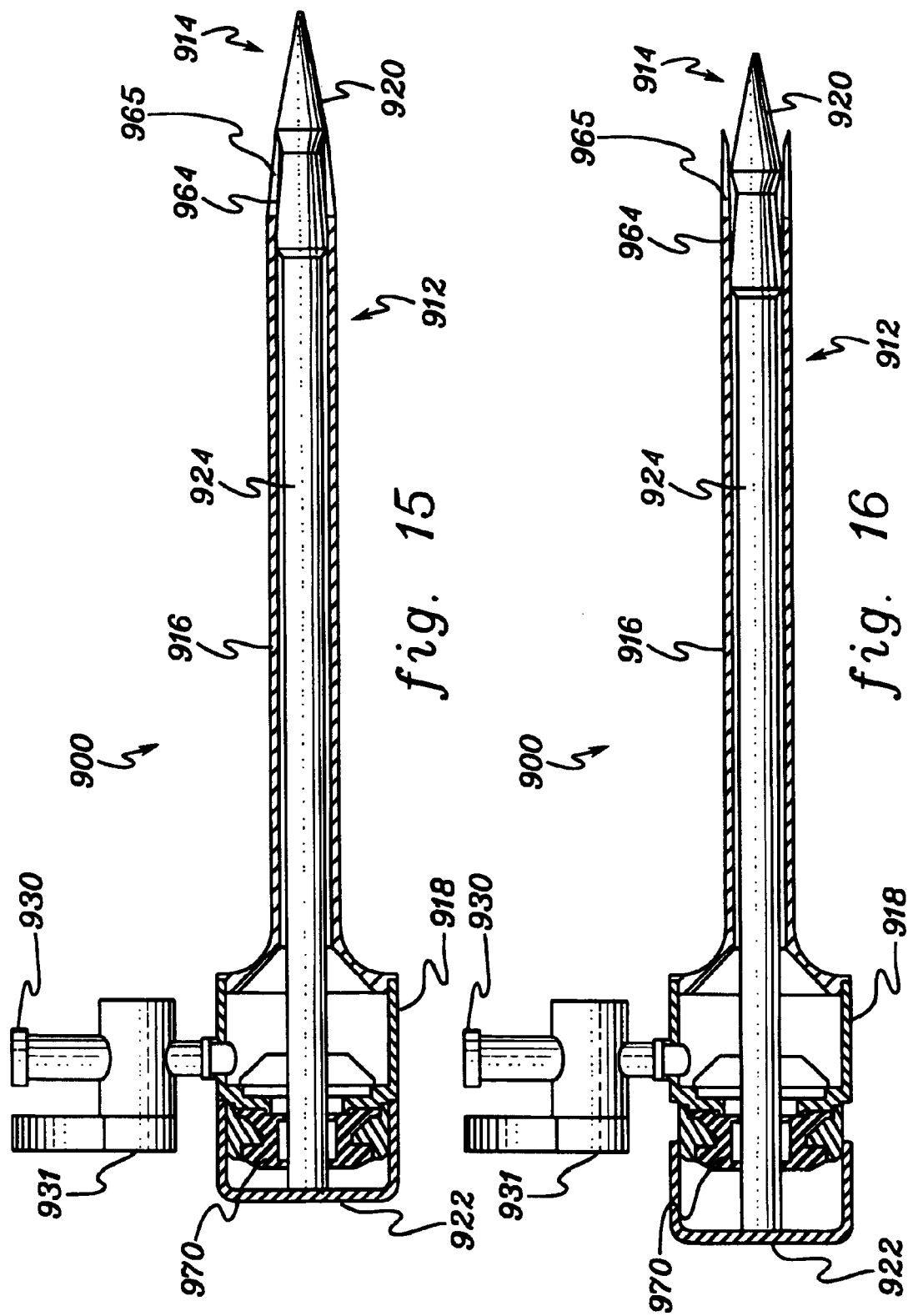

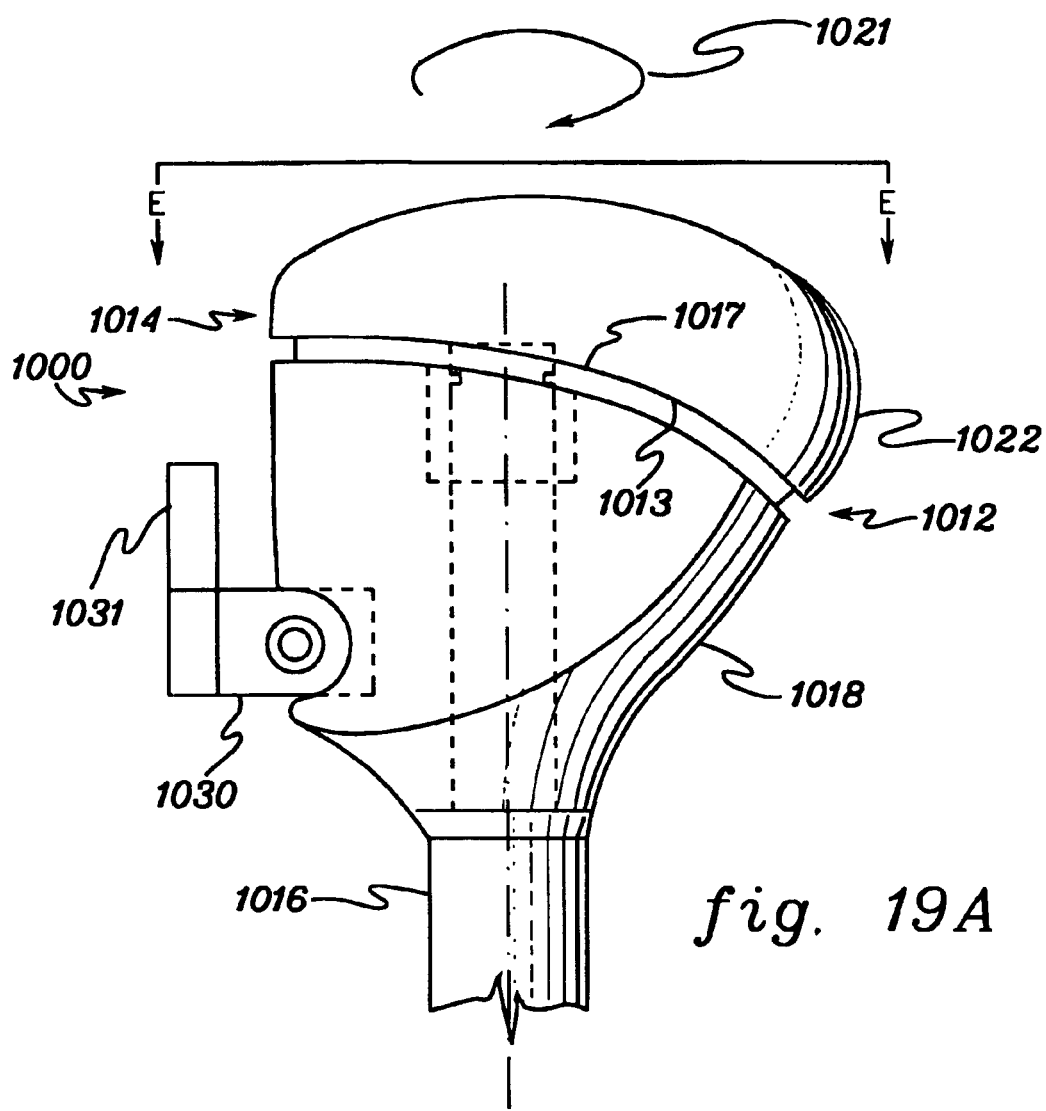
fig. 19A
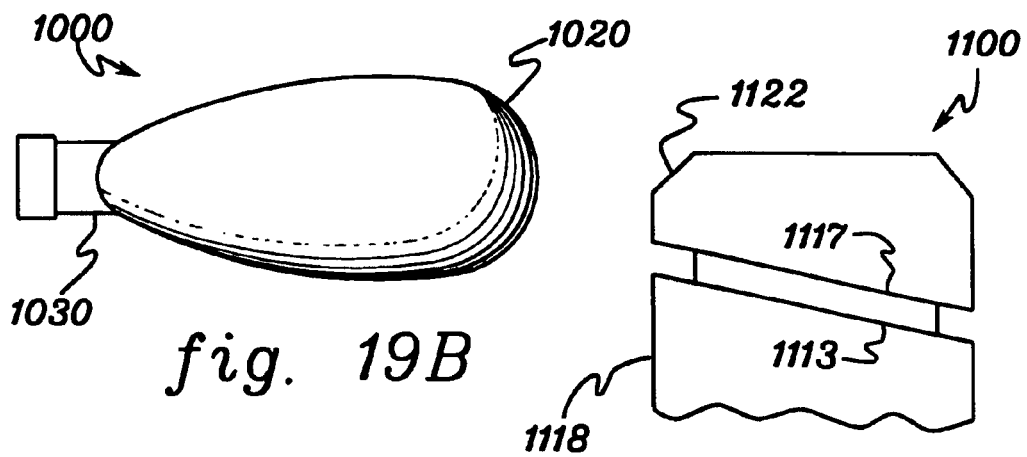
fig. 19B
fig. 19E

OBTURATOR AND CANNULA FOR A TROCAR ADAPTED FOR EASE OF INSERTION AND REMOVAL

TECHNICAL FIELD

This invention relates generally to surgical instruments, and more particularly to apparatus and methods used for providing an opening for inserting surgical instruments through tissue and into body cavities.

BACKGROUND OF THE INVENTION

A trocar-cannula, or simply, a trocar, is a surgical device used to obtain access to a body cavity to perform various surgical procedures, for example, laparoscopic surgery or arthroscopic surgery. The trocar is an elongated, pointed surgical instrument having a pointed rod-like device, referred to in the art as an "obturator", that is fitted into a tube-like device that is referred to in the art as a "cannula". The pointed, sometimes sharply pointed, end of the obturator projects out the end of the cannula and is used to penetrate the outer tissue of the cavity. After the tissue is penetrated and the body cavity, for example, is accessed by the trocar, the obturator is withdrawn from the cavity and the cannula is left in place in the cavity to provide a channel for accessing the cavity. The body cavity can then be accessed by further surgical instruments via the cannula to perform various surgical procedures, or the cannula can simply be used as a drainage outlet. Among other uses, trocar devices are typically used to penetrate the human abdominal wall to gain access, for example, to the organs within.

One prior art trocar is the device disclosed in commonly-assigned U.S. Pat. No. 5,824,002. This patent discloses a "transition-less" trocar, that is, a trocar which provides a smooth geometric transition between the tip of the obturator to the end of the cannula so that the trocar can be inserted with reduced force compared to trocars having an abrupt geometric transition while reducing the potential for damaging tissues. However, there is still a need in the art to further reduce the potential for damaging tissue, sutures, and the instruments themselves and there is still a need to further reduce the force and effort that need be exerted by the surgeon.

These and other desirable features for trocars and their use compared to the prior art are provided by the present invention and will become readily apparent upon review of the following summary, detailed description, and claims.

SUMMARY OF THE INVENTION

Due to the delicate nature with which a trocar is used, it is highly desirable to minimize the damage to surrounding tissue and organs during the insertion and removal of the trocar. Thus, one goal of the present invention is to provide a trocar and a method of using a trocar which minimizes or eliminates the potential for damaging tissues or organs when using a trocar. Another desirable feature of a trocar is that it require as little force or effort by the surgeon as possible while using the trocar. Thus, another goal of the present invention is to provide a trocar and method of using a trocar that requires less force and effort by the surgeon using a trocar. In addition, another aspect of the present invention provides a more stable placement of the cannula in the patient, that is, the placement of the cannula in the patient is less likely to be moved or disturbed compared to prior art methods and devices.

The present invention provides methods and apparatus which address many of the limitations of prior art methods and apparatus. Though the term "trocar" and "obturator" are sometimes used interchangeably to refer to the pointed instrument that is inserted into the cannula, in the following discussion the term "trocar" will be reserved for the combined obturator-cannula assembly and the term obturator will be used to refer to the pointed device that is inserted into the cannula.

One aspect of the present invention is an obturator for use with a cannula having a bearing surface, the obturator including an elongated shaft having a first end, a second end, and an axis directed along the direction of elongation of the shaft; and a cap assembly mounted at the second end, the cap assembly having at least one bearing surface adapted for slidably engaging the bearing surface of the cannula wherein the obturator is deflected relative to the cannula. The bearing surface on the cap assembly is typically a surface inclined with respect to the axis of the shaft, but the bearing surface on the cap assembly may also be essentially parallel or perpendicular to the axis of the shaft The bearing surface of the cap assembly may be the surface of a projection or the surface of a recess in the cap assembly. Also, the at least one bearing surface of the cap assembly may be at least two bearing surfaces. The cap assembly may take any appropriate cross-sectional shape, for example, rectangular, triangular, circular, or ellipsoidal in coss-section, among others, but preferably the cap assembly is circular or rectangular in shape.

Another aspect of the present invention is a trocar, including a cannula having a first end and a second end, the second end having at least one first bearing surface; an obturator comprising an elongated shaft having a pointed end and an end having a cap assembly having at least one second bearing surface adapted to cooperate with the first bearing surface; and means for slidably engaging the first bearing surface and the second bearing surface whereby the obturator is deflected relative to the cannula. The means for slidably engaging the first bearing surface and the second bearing surface may comprise rotating the obturator relative to the cannula. The first bearing surface and the second bearing surface may comprise inclined surfaces whereby rotating the obturator relative to the cannula slidably engages the surfaces and axially deflects the obturator relative to the cannula. One or more of the bearing surfaces may be linear or curvilinear in shape. The first bearing surface and the second bearing surface may comprise a projection, a recess, a boss, or combinations thereof.

Another aspect of the present invention is a method for removing a trocar obturator from tissue, the method comprising: rotating the obturator within and relative to a cannula to engage respective surfaces of the obturator and the cannula so as to deflect the obturator relative to the cannula; and extracting the obturator from the tissue by withdrawing the obturator through the cannula. The trocar typically includes a cannula having at least one first bearing surface and the obturator includes a cap assembly having at least one second bearing surface adapted to cooperate with the first bearing surface, wherein at least one of the first bearing surface and the second bearing surface comprise an inclined surface, further comprising slidably engaging the first bearing surface against the second bearing surface during the rotation to thereby axially deflect the obturator at least partially out of the tissue. When rotating the obturator, the obturator is typically rotated at least about 5 degrees and preferably at least about 15 degrees relative to the cannula. In one aspect of the invention, the obturator is rotated about 90 degrees, and may be rotated further.

This aspect of the invention not only minimizes the potential for damaging tissues or organs and reduces the effort exerted by the surgeon, but also provides a more stable placement of the cannula in the patient. For example, in prior art methods in which the surgeon typically must physically restrain the cannula while extracting the obturator, the placement of the obturator within the patient may be disturbed, for instance laterally or axially, as the surgeon extracts the obturator. This handling and movement of the cannula by the surgeon can undesirably deflect the cannula and may damage adjacent tissue or sutures, for example, sutures used to restrain the cannula. However, in this aspect of the invention, disturbing the placement of the cannula is minimized or eliminated. The relatively little effort required to rotate the obturator within the cannula whereby the mating bearing surfaces bear against each other and deflect the obturator, according to this aspect of the present invention, requires far less physical restraint of the cannula by the surgeon and thus far less likelihood of disturbing the placement of the cannula than prior art methods and devices.

A further aspect of the present invention is a cannula for a trocar, the cannula including an elongated cylindrical tube having a first inside diameter, an open first end, and an open second end adapted for receiving an obturator; and wherein the open first end is flexible and internally tapered from the first inside diameter to a second inside diameter, smaller than the first inside diameter, the second inside diameter being smooth and continuous. The tube may also have a first outside diameter and the open first end of the tube is externally tapered from the first outside diameter to a second outside diameter, smaller than the first outside diameter. The second inside diameter of the tube may also be essentially the same as the second outside diameter. In addition, the material of the open first end of the tube may be a thermoplastic polymer or a thermoset polymer. The tube may have an inside diameter of essentially uniform diameter. The tube may have any appropriate cross-sectional shape, but is preferably circular in cross-section. The open second end may include a flexible seal, for example, a seal which permits the passage of the obturator with little or no fluid leakage.

An additional aspect of the present invention is a trocar including an obturator having an elongated shaft with an axis and an outside diameter; a first end having a tip adapted for insertion into tissue, the first end having a maximum diameter; and a second end; and a cannula having an open first end having an inside surface and a first inside diameter, and an open second end adapted for receiving the obturator; wherein the inside surface of the first end of the cannula is flexible and the first inside diameter of the first end of the cannula is smaller than the maximum diameter of the first end of the obturator. The inside surface of the first end of the cannula may be uniformly tapered from a second inside diameter, larger than the first inside diameter, to the first inside diameter. Also, the first inside diameter of the first end of the cannula is preferably smooth and continuous, having no slots or other interruptions, though in one aspect of the invention one or more axial slots may be present. The first end of the obturator may also include a first tapered surface extending from the maximum diameter of the first end to the tip. Also, the first end of the obturator may include a second tapered surface extending from the maximum diameter to the outside diameter of the shaft.

A still further aspect of the present invention is a method for removing an obturator from a trocar, the method including: providing an obturator having an elongated shaft and a tip, the tip having a first diameter; providing a cannula having an elongated tube, the tube have a flexible and continuous open end having an inside diameter, the inside diameter being less than the first diameter of the tip of the obturator; holding the cannula in a relatively stationary position; radially deflecting the open end of the cannula to increase the inside diameter of the open end; passing the tip of the obturator through the increased inside diameter of the open end of the cannula; and withdrawing the obturator from the cannula. The step of radially deflecting the open end of the cannula may include impinging the tip of the obturator against the inside diameter of the open end of the cannula. This radial deflection of the open end of the cannula may be an elastic or plastic deflection. Also, the cannula may further include at least one first bearing surface and the obturator may further include at least one second bearing surface adapted to cooperate with the first bearing surface, wherein the radially deflecting the open end of the cannula comprises: rotating the obturator relative to the cannula, slidably engaging the first bearing surface against the second bearing surface whereby the obturator is deflected relative to the cannula, and impinging and deflecting the inside diameter of the open end of the cannula with the tip of the obturator.

Another aspect of the present invention is a trocar including a cannula having a first end and a second end, the first end having a smooth and continuous outside surface and an inside diameter, the second end having a head assembly, the head assembly having at least one first bearing surface; and an obturator comprising a shaft, a first end having a tip, a second end, and an axis directed along the direction of elongation of the shaft; the first end of the obturator having a maximum diameter, a first tapered surface extending from the maximum diameter to the tip, and a second tapered surface extending from the maximum diameter to the outside diameter of the shaft; the second end of the obturator having a cap assembly, the cap assembly having at least one second bearing surface adapted for slidably engaging the first bearing surface of the cannula head assembly; wherein at least one of the first bearing surface and the second bearing surface is inclined relative to the axis of the obturator; wherein when the obturator is rotated about its axis relative to the cannula, the second bearing surface slidably engages the first bearing surface and axially deflects the obturator whereby the second tapered surface of the first end of the obturator impinges and deflects the inside diameter of the first end of the cannula and the maximum diameter of the obturator can pass through the open first end of the cannula and the obturator can be removed. The head assembly may include a flexible seal which permits the passage of the obturator with little or no fluid leakage, for example, little or no leakage of treatment or bodily liquids or gases.

An even further aspect of the present invention is a method of using a trocar, the trocar comprising an obturator having a tip and a cannula having a flexible open end, the method of including: inserting the trocar into a body cavity; slidably engaging a bearing surface on the cannula against a bearing surface on the obturator thereby deflecting the obturator relative to the cannula; impinging the tip of the obturator against an open end of the cannula and enlarging the open end of the cannula; passing the tip of the obturator through the enlarged open end of the cannula; and withdrawing the obturator from the cannula. The step of slidably engaging the bearing surfaces may be practiced by rotating the obturator relative to the cannula. The bearing surface on the cannula or on the obturator may be moveable relative to the cannula or obturator, respectively. For example, the bearing surfaces on the cap assembly or obturator may be the surface of a wedge, a lever, a cam, a bar, a linkage, and a screw, among other things. This method may also include the further step of passing surgical instruments through the cannula into the body cavity. Also, the deflection of the obturator relative to the cannula is typically an axial deflection and the axial deflection typically deflects the obturator out of the body cavity.

A still further aspect of the present invention is a cannula for use with an obturator, the cannula including a cylindrical tube having a first end and a second end; a head assembly mounted to the first end of the cylindrical tube; and a resilient sealing element mounted in the head assembly having at least one aperture; whereby when the obturator is inserted into the cannula, the obturator passes through the at least one aperture in the sealing element whereby little or no fluid escapes from the cannula to the ambient environment. In one aspect of the invention, the at least one aperture is at least two apertures. In another aspect of this invention, the sealing element includes at least one membrane and the at least one aperture comprises a slit in the membrane. The sealing element is typically made from a resilient or elastomeric material, for example, silicone rubber, polyurethane elastomer, neoprene or thermo plastic elastomer.

Thus, the present invention provides an obturator, a cannula, a trocar and methods of using an obturator, a cannula, or a trocar which minimize or eliminate the potential for damaging tissues or organs, reduce the force or effort a surgeon must exert when using such devices, and minimize the potential for ensnaring or damaging sutures, tissues, other instruments, or the obturator, cannula, or trocar itself. These and other advantages, embodiments, and aspects of the present invention will become more apparent upon review of the attached drawings, the description below, and the attached claims.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed descriptions of the preferred embodiments and the accompanying drawings in which:

FIGS. 10A and 10B illustrate the geometry of the end of the trocar shown in FIG. 1 according to another aspect of the present invention.

FIGS. 11A through 11D illustrate further alternative aspects of the trocar cap assembly and the cannula head assembly according to the present invention.

FIGS. 12A through 12D illustrate further alternative aspects of the trocar cap assembly and the cannula head assembly according to the present invention.

FIG. 15 is a partial cross-sectional view of the device shown in FIGS. 13 and 14.

FIG. 16 is a partial cross-sectional view illustrating the operation of the device shown in FIGS. 13 through 15.

FIGS. 19A through 19C are a side view, top view, and perspective view of a trocar according to another aspect of the invention.

FIG. 19E is a side view of an alternative aspect of the invention shown in FIG. 19A.

DETAILED DESCRIPTION OF THE PREFERRED EMBODIMENTS

Figure 1:
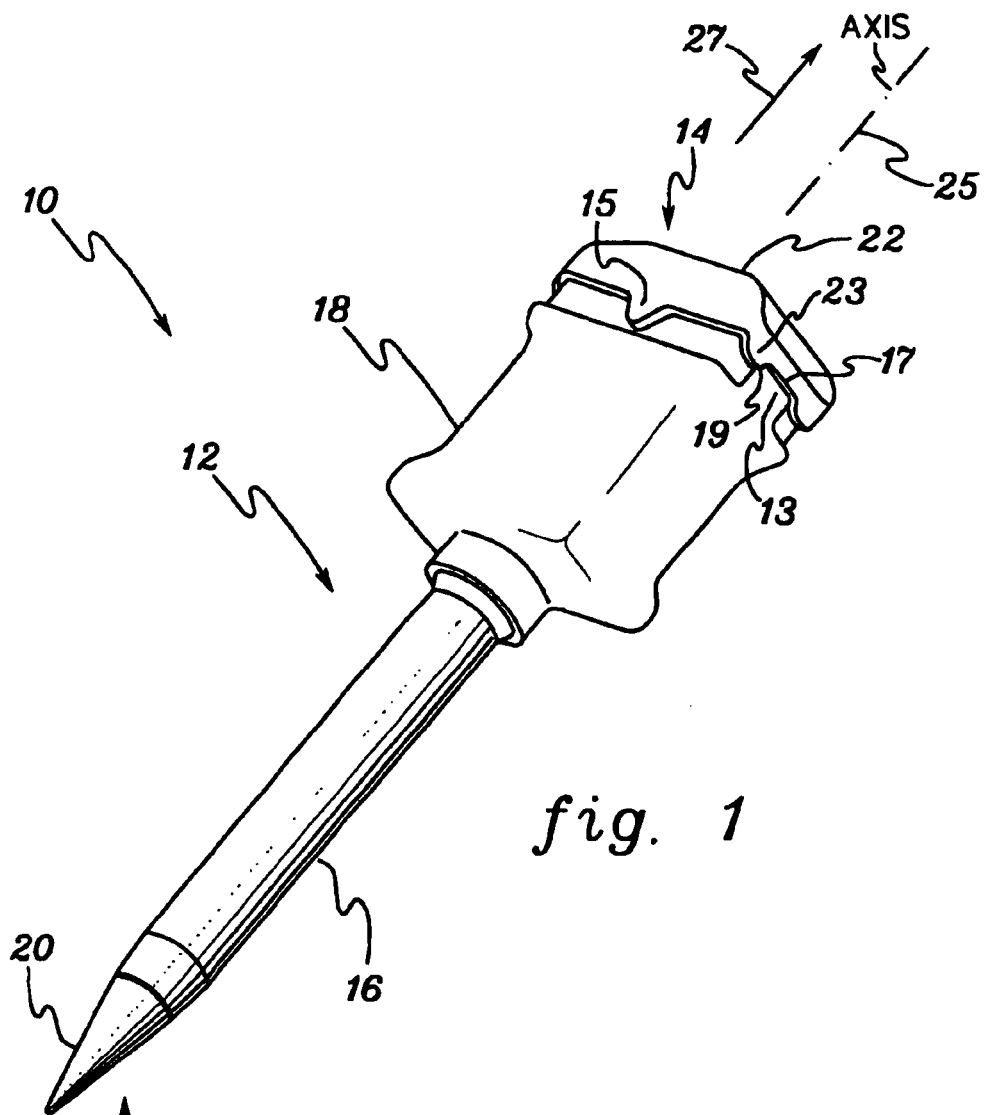
FIG. 1 is a perspective view of a trocar according to one aspect of the present invention.

FIG. 1 illustrates a perspective view of a trocar 10 embodying one aspect of the present invention. This aspect of the invention includes a cannula assembly 12 and an obturator 14. Cannula assembly 12 includes a cannula tube section 16 and a cannula head assembly 18. Obturator 14 includes pointed tip 20, a cap assembly 22, and a shaft 24 (shown in FIG. 3) between pointed tip 20 and cap assembly 22. Cannula tube 16 comprises an essentially hollow tube in which obturator 14 is inserted prior to surgery and from which obturator 14 is withdrawn after insertion into the body cavity. Cannula head assembly 18 is typically adapted to be held by the surgeon, for example, during insertion of trocar 10 or withdrawal of obturator 14. Cannula head assembly 18 may also provide means for introducing one or more gases through the cannula, for example, for insufflating a body cavity when providing a pneumoperitoneum. Obturator cap assembly 22 typically provides a surface upon which the surgeon can push when inserting the trocar 10 through the tissue being penetrated and also provides a means for grasping obturator 14 when removing obturator 14.

One aspect of the present invention illustrated in trocar 10 is the interrelationship between the geometry of cannula head assembly 18 and cap assembly 22 which aids in the removal obturator 14 from cannula assembly 22. According to this aspect of the invention, head assembly 18 includes at least one bearing surface 19 and cap assembly 22 includes at least one bearing surface 23 that impinge upon each other when cap assembly 22 is rotated about its axis, indicated by line 25 in FIG. 1, whereby obturator 14, that is, the tip 20, shaft 24, and cap assembly 22, is axially deflected, in the direction generally indicated by arrow 27. Bearing surfaces 19, 23 are typically located on bosses 13, projections 15, or recesses 17 in the cap assembly 22 or head assembly 18. As shown in FIG. 1, these at least one bearing surfaces 19, 23 on bosses 13, projections 15, or recesses 17 may be two or more bearing surfaces located along any side of head assembly 18 and the cap assembly 22, and may even be located on the top surface of head assembly 18 and the bottom surface of cap assembly 22. For example, for the rectangular cap assembly 22 shown in FIG. 1, recesses 17 are located along either end of cap assembly 22, bosses 13 are also located along either end of cannula head assembly 18 and projections 15 are located along the sides of cap assembly 22. Cap assembly 22 shown in FIG. 1 is rectangular in shape, but cap assembly 22 may take any shape including circular, square, or ellipsoidal, among others. Regardless of the shape of the cap assembly 22 and head assembly 18 and the number, location, and shape of bosses 13, projections 15, and recesses 17, the same function is effected, that is, obturator 14 can be axially deflected relative to cannula 12 when rotated about its axis 25. Such a configuration provides a relatively convenient means of removing obturator 14. Though in the aspect shown in FIG. 1, obturator 14 is shown deflecting in the direction generally indicated by arrow 27, the present invention may also be implemented in such a way that obturator 14 is deflected in a direction opposite to arrow 27, if desired. For example, to aid in the insertion of obturator 14 through the skin of the patient.

Figure 2:
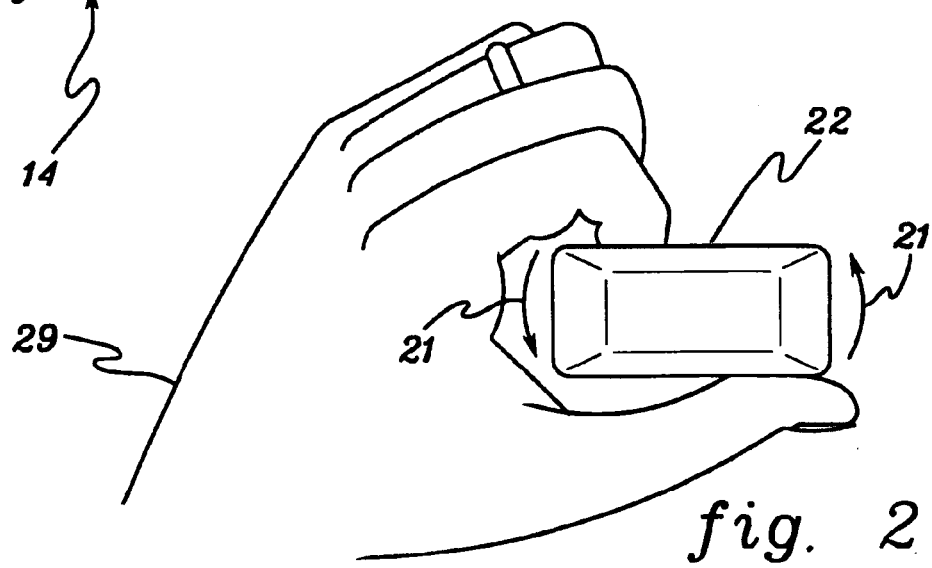
FIG. 2 is a top view of the trocar device shown in FIG. 1.

The axial deflection of obturator 14 provides an effective means of removing obturator 14 from the tissue into which it is inserted. The manual rotation of the obturator cap assembly 22 is illustrated in FIG. 2 in which a hand 29 of a surgeon is shown in the act of rotating cap assembly 22 in the direction indicated by arrows 21. Typically, cannula assembly 12 is restrained from moving while cap assembly 22 is rotated, for example, restrained by the other hand of the surgeon. This rotation, though preferably performed manually by the surgeon, can also be automated and performed remotely, for example, by a computer-controlled servomechanism.

Figure 3:
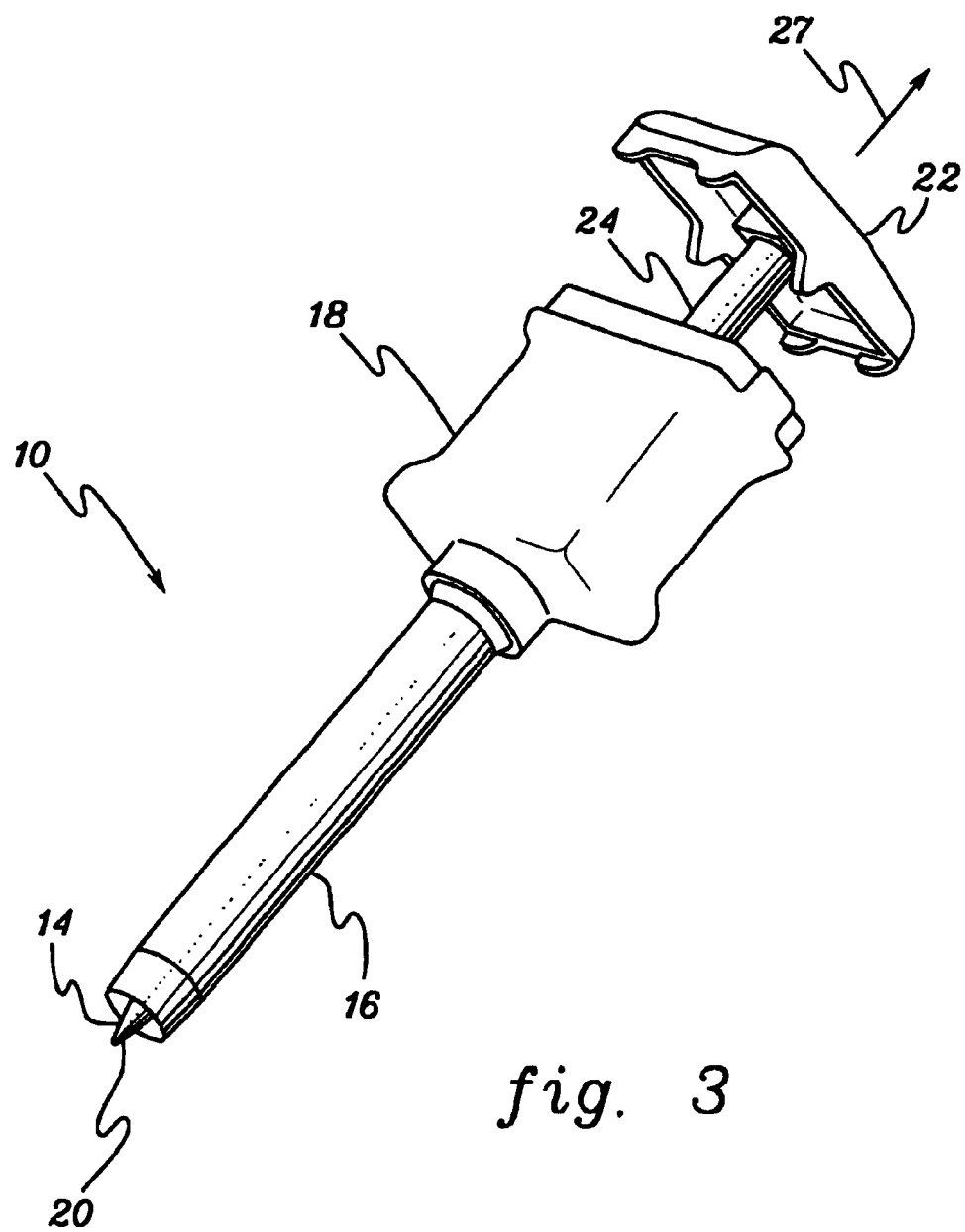
FIG. 3 is a perspective view of the trocar shown in FIG. 1 in which the obturator is being removed from the cannula.

Trocar 10 and the relative displacement of obturator 14 with respect to cannula 16 and cannula head assembly 18 shown in FIG. 1 are illustrated in FIG. 3. After cap assembly 22 is rotated, as shown in FIG. 2, and deflected according the present invention, obturator 14 can be removed from cannula 16 as generally shown in FIG. 3 by arrow 27. Also shown in FIG. 3 is obturator shaft 24 which extends from obturator tip 20 to obturator cap assembly 22.

Figure 4A:
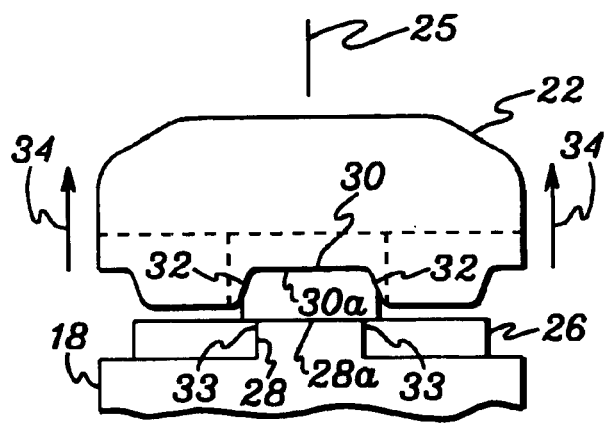
FIGS. 4A through 4D illustrate various alternative aspects of the trocar cap assembly and the cannula head assembly according to the present invention.

The bearing surfaces on cap assembly 22 may take various forms, some of which are illustrated in FIGS. 4A through 4D. FIG. 4A illustrates a side view of cap assembly 22 a partial view of head assembly 18 shown in FIG. 1. Only the top of head assembly 18 is shown in this figure. Cap assembly 22 includes a central axis 25 which corresponds to the axis of, for example, obturator 14 (not shown). According to this aspect of the invention, head assembly 18 and cap assembly 22 include at least one set of cooperating surfaces that bear against each other, preferably at an angle, to promote sliding engagement and axial deflection of obturator 14 relative to cannula head 18 and cannula 12. In the aspect of the invention shown in FIG. 4A, head assembly 18 includes an annular recess 26 which is interrupted by at least one boss 28, preferably at least two bosses 28. Boss 28 may take many geometric forms and still effect the desired function, for example, boss 28 may have a rectangular shape, as shown in FIG. 4A, or semi-circular, semi-ellipsoidal, trapezoidal, triangular, conical, parabolic, hyperbolic, or any other smooth curve or polygonal shape. Cap assembly 22 includes at least one recess 30, again, preferably, at least two recesses 30 which is shaped to cooperate with boss 28. Again, recess 30 may take many geometric forms, such as the trapezoidal shape shown in FIG. 4A, or any of the shapes or contours described above for boss 28.

According to this aspect of the invention, either boss 28 or recess 30 include at least one inclined surface or ramp. For example, in FIG. 4A, recess 30 includes two inclined surfaces 32 which can bear against the sides 33, for example, the corners, of boss 28. The one or more surfaces 32 are typically inclined at an angle of about 45 degrees to the axis 25, but may be inclined at any angle between about 10 degrees and about 80 degrees, and are preferably between about 30 degrees to about 60 degrees to the axis 25. Typically, cap assembly 22 and head assembly 18 include at least two mating surfaces 32, 33 located on opposite sides of cap assembly 22 to provide a relatively balanced upward thrust on obturator cap 22 of obturator 14 relative to cannula 12. As noted, above the thrust effected by the mating surfaces may also provide a downward thrust.

In operation, when obturator 14 is inserted into cannula assembly 12, the surface 30a of recess 30 contacts the surface 28a of boss 28, though a clearance may also be present between surface 30a and surface 28a. According to this aspect of the invention, when the surgeon rotates cap assembly 22 relative to cannula 12, for example, as shown in FIG. 2, at least one inclined surface 32 of recess 30 impinges and slidably engages boss 28 whereby the cap assembly 22 is axially deflected as indicated by arrows 34. This upward thrust of obturator 14, though slight, can provide sufficient force and displacement to disengage the tip 20 of obturator 14 from the tissue, for example, into which obturator 14 is inserted.

Figure 4B:
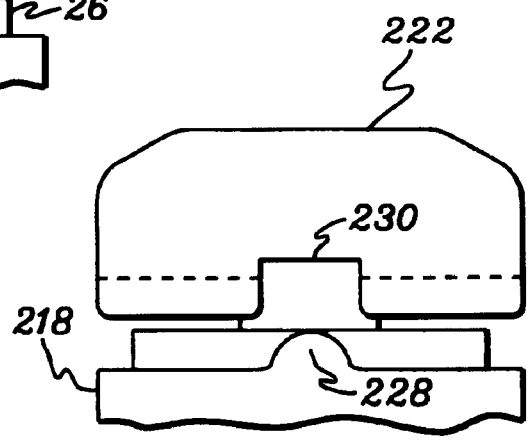
Figure 4C:
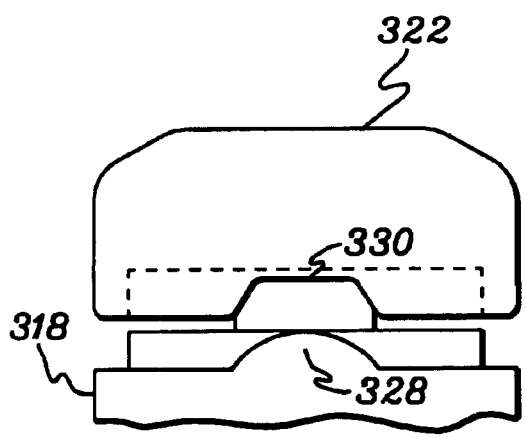
Figure 4D:
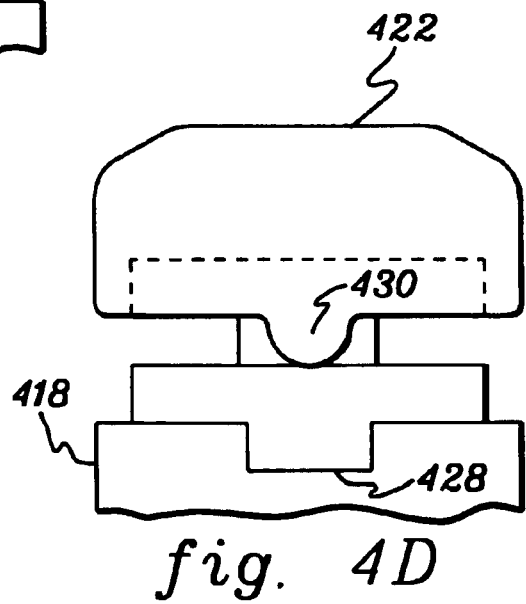

Alternative bearing surface configurations that can be used on head assembly 18 and cap assembly 22 are illustrated in FIGS. 4B through 4D. FIG. 4B illustrates an obturator cap 222 having at least one rectangular recess 230 and a cannula head assembly 218 having at least one semicircular boss 228. FIG. 4C illustrates an obturator cap 322 having at least one semi-ellipsoidal boss 328 and a cannula head assembly 318 having at least one trapezoidal recess 330. FIG. 4D illustrates an obturator cap 422 having at least one semi-circular projection 430 and a cannula head assembly 418 having at least one rectangular recess 428. As described with respect to FIG. 4A, the respective bosses and recesses of FIGS. 4B through 4D slidably engage and axially deflect obturator 14 when obturator cap assembly 22, 222, 322, 422, is rotated about its respective axis while cannula assembly 12 is held generally stationary. Of course, many other combinations of bosses, projections, and recesses may be used to effect the desired sliding engagement and axial deflection.

Figure 5A:
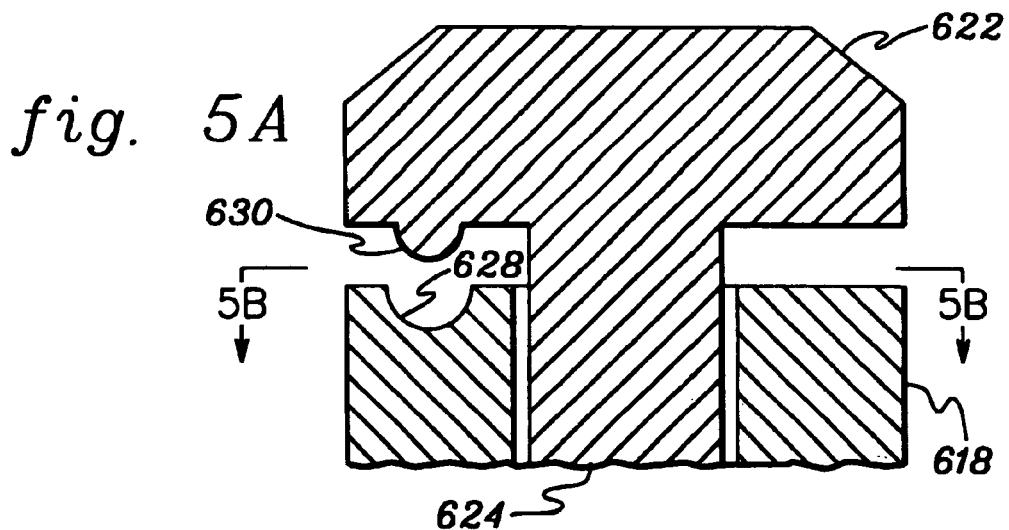
FIGS. 5A through 5C illustrate further alternative aspects of the trocar cap assembly and the cannula head assembly according to the present invention.
Figure 5B:
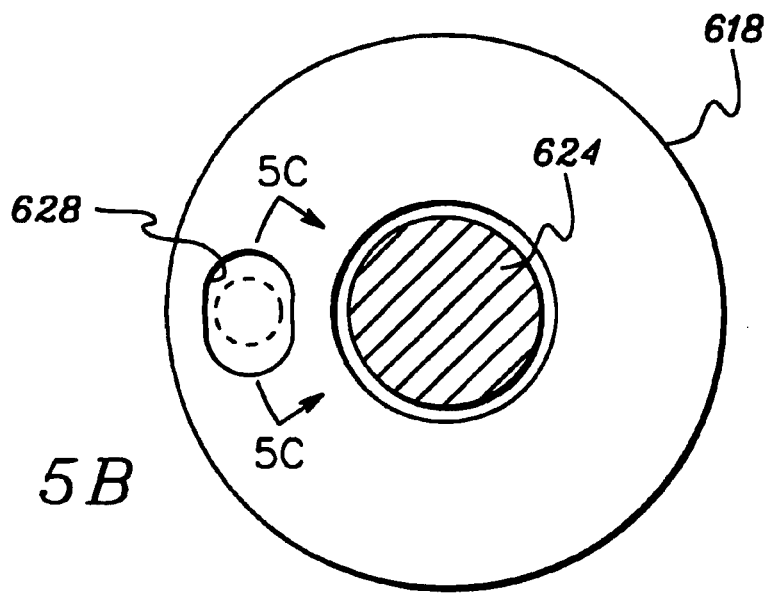
Figure 5C:
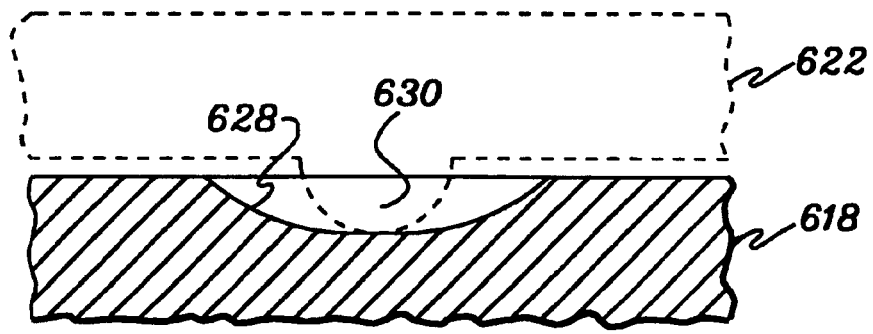

Further aspects of the present invention are illustrated in FIGS. 5A through 5C. FIG. 5A illustrates a cross-section of an obturator cap 622 having at least one semi-circular projection 630 and a cross-section of a cannula head assembly 618 having at least one semi-circular recess or slot 628. Obturator cap 622 is attached to obturator shaft 624. The sectional view 5B—5B identified in FIG. 5A is shown in FIG. 5B. As shown in FIG. 5B, recess 628 is a slot, for example, a circumferential slot, having rounded ends. The cross-section of slot 628 as indicated by sectional view 5C—5C is shown in FIG. 5C. The obturator cap 622 and projection 630 are shown in phantom in FIG. 5C. As shown in FIG. 5C, slot 628 includes inclined ends that act as surfaces upon which semi-circular projection 630 can bear when obturator cap 622 is rotated relative to cannula head assembly 618. According to this aspect of the invention, the rotation of cap 622 causes the surface of projection 630 to bear against and ride up on either inclined surface of slot 628 and, in so doing, axially deflect obturator cap 622. The axial deflection of obturator cap 622 axially deflects obturator shaft 624 as desired according to the present invention.

Though the bearing surfaces illustrated in FIGS. 1, 3, 4A through 4D, and FIGS. 5A through 5C include bosses, projections, and recesses, among other things, it will be apparent to those of skill in the art that other forms of geometric constructions can also be used to provide the desired deflection. For example, the bearing surfaces may comprise threaded surfaces, for example, course (UNC), fine (UNF), pipe (NPT), or acme-type threads. The bearing surfaces may also be provided by gear teeth, splines, cams and cam followers, bearings (ball, roller, or needle), among other bearing surfaces. For example, further aspects of the present invention which provide axial deflection of the obturator relative to the cannula are shown and will be discussed below in reference to FIGS. 11A through 11D, FIGS. 12A through 12D, FIGS. 13 through 16, and FIGS. 19A through 19E.

Though the aspects of the invention illustrated in FIGS. 4A through 4D and FIGS. 5A through 5C provide effective means for axially deflecting obturators and thereby facilitating removal of obturators from body cavities, as will be discussed below, this aspect of the invention can be combined with the aspect disclosed in FIGS. 10A and 10B to provide an even more advantageous device and method.

Figure 6:
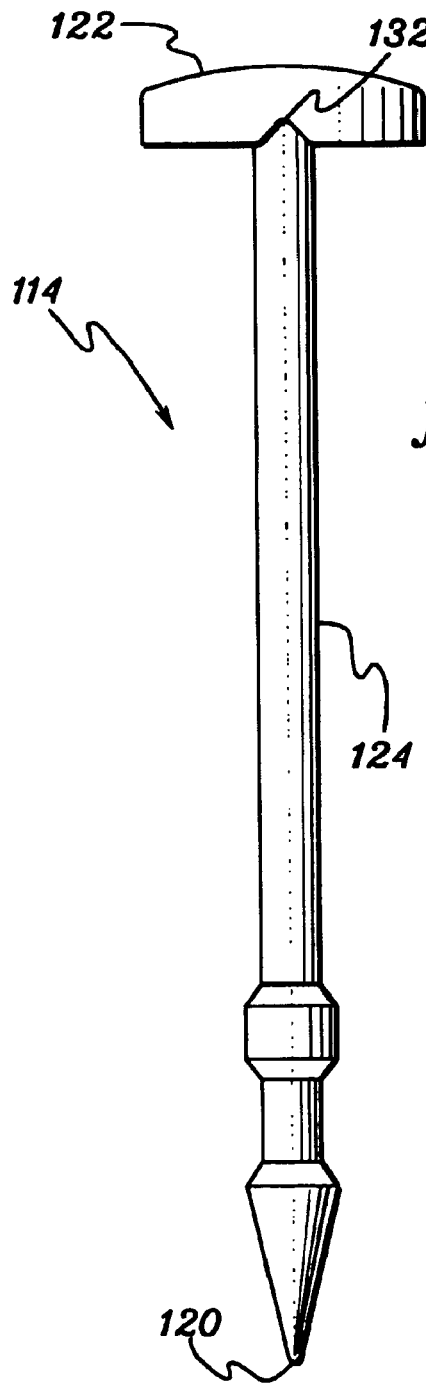
FIGS. 6 and 7 are a side elevation view and a perspective view, respectively, of an obturator according to another aspect of the present invention.
Figure 7:
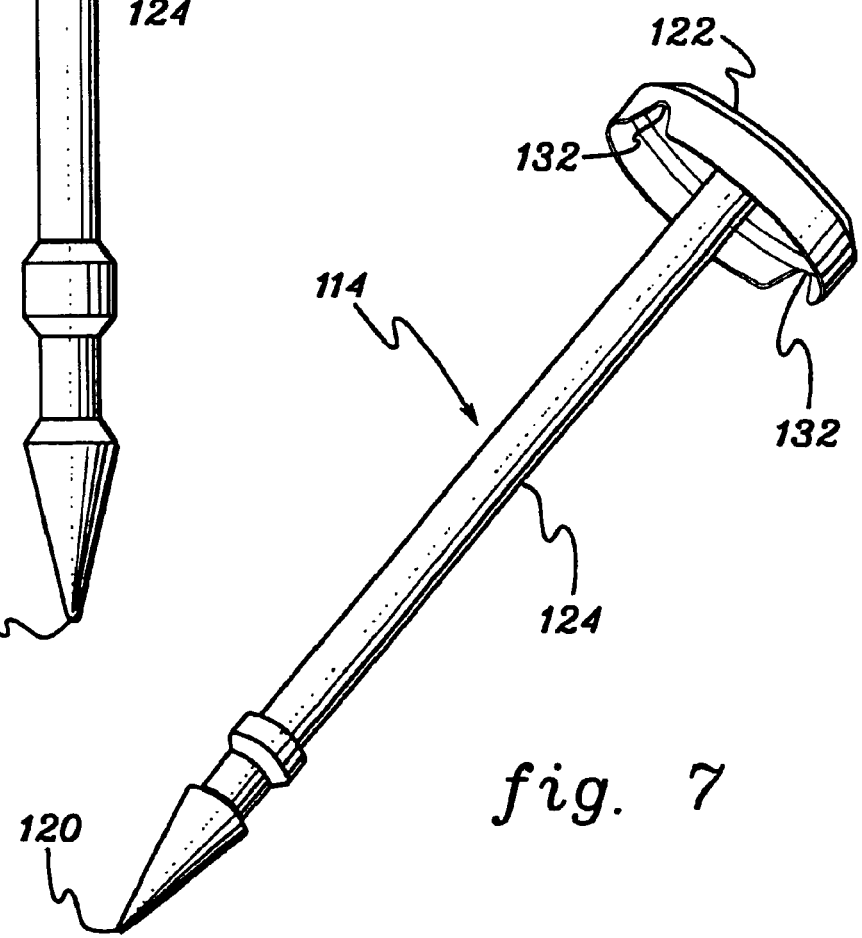

Further aspects of the present invention are shown in FIGS. 6 through 9. FIGS. 6 and 7 illustrate an obturator 114 having a shaft 124, a tip 120, and a circular cap assembly 122. Obturator 114 may comprise one integral piece, for example, an integral metal piece made of, for example, stainless steel, titanium, or aluminum. Obturator 114 may also be comprised of two or more individual components of the same or dissimilar materials. For example, cap assembly 122, shaft 124, and tip 120 may be formed from individual pieces and then assembled, for example, by means of mechanical fastening, for example, via threaded connections. In addition, cap assembly 122 may be made of plastic having a threaded connector, having internal or external threads, and shaft 124 may be made of stainless steel having a threaded end which engages the threaded connector of cap 122. Tip 120 may also be a individual steel part which is threaded either internally or externally to shaft 124. Other modes of assembly will be apparent to those of skill in the art. Cap assembly 122 typically includes two diametrically-opposed triangular-shaped recesses 132 that can be used to effect the axial deflection which characterizes one aspect of the present invention as described above.

Figure 8:
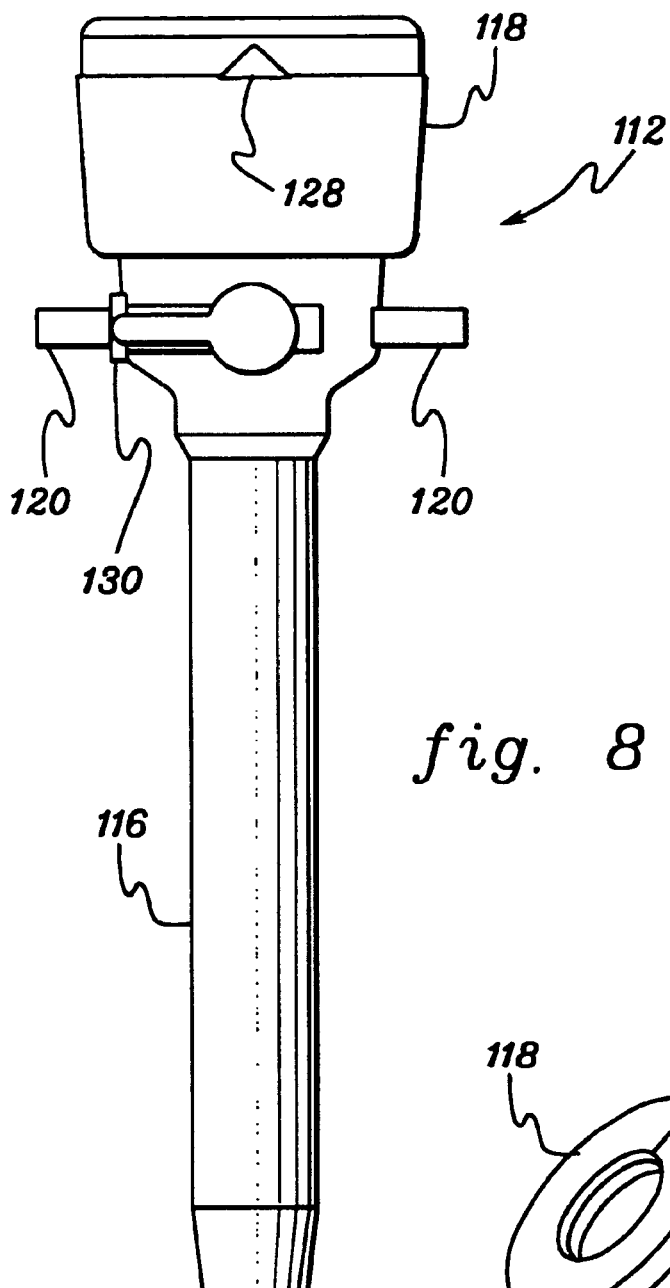
FIGS. 8 and 9 are a side elevation view and a perspective view, respectively, of another cannula assembly according to the present invention.
Figure 9:
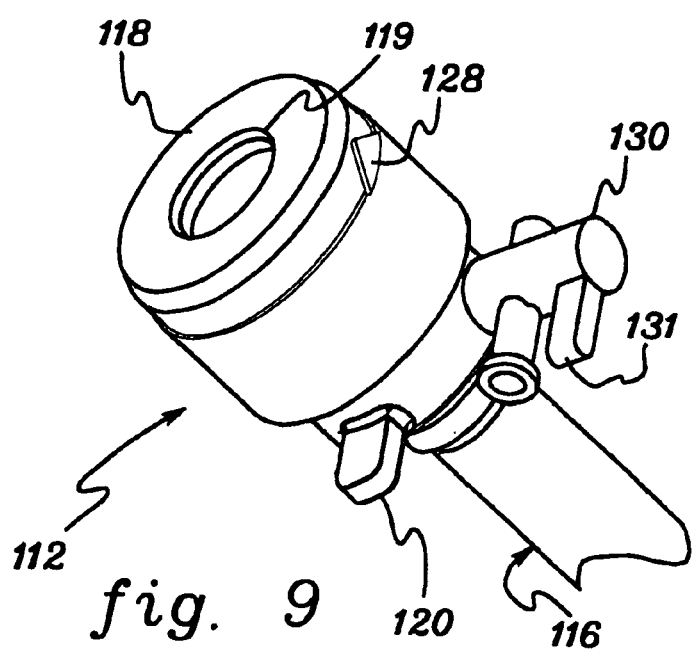

FIGS. 8 and 9 illustrate a corresponding cannula assembly 112 having cannula tube 116 and circular cannula head assembly 118 having triangular-shaped protrusions or bosses 128. Triangular-shaped bosses 128 may cooperate with triangular-shaped recesses 132 of obturator cap 122 of FIG. 6 to effect the slidable engagement and axial deflection discussed above. As is typical in the art, cannula head assembly 118 may include one or more handles 120 and a gas supply port 130. Handles 120 provide a means for grasping the trocar assembly during insertion and removal. Of course, the general shape of cannula assembly 112 may provide sufficient means for grasping the trocar and in one aspect of the invention no clearly defined handles may be provided. Gas supply port 130 communicates with the inside of cannula tube 116 to provide a source of gas to the body cavity, for example, for insufflation. Port 130 may include a valve 131, for example, a hand-operated valve. Valve 131 may be used to introduce or remove fluids, that is, gases or liquids, from the body cavity. For example, valve 131 may include a vent position to vent gases from the body cavity to the ambient atmosphere. Head assembly 118 in FIG. 9, in addition to the triangular bosses 128, handles 120, gas supply port 130 shown in FIG. 8, illustrates an opening 119 in the top of head assembly 118 through which obturator 114 is typically inserted and removed.

FIGS. 10A and 10B illustrate another aspect of the present invention that can be present in trocar 10 of FIGS. 1 and 2 and in obturator 114 and cannula assembly 116 of FIGS. 6 through 9. The items in FIG. 10A are numbered to correspond to the embodiment illustrated in FIG. 1. FIG. 10A illustrates a detailed view, partially in cross-section, of tip 20 of obturator 14 and the distal end of cannula tube 16 of, for example, trocar 10 of FIG. 1. Obturator 14 includes a shaft 24 having a diameter 41. Tip 20 includes a conically-tapered end 42 that tapers from a diameter 44, typically a maximum diameter of obturator 14, to a point 46, typically a rounded point though point 46 may be a sharp point. Tapered tip 20 is designed to permit relatively easy insertion of trocar 10 through, for example, the muscle and facia of a patient and into a body cavity with minimal force and minimal damage to the tissue penetrated and minimal damage to the internal tissues and organs. The surfaces of tapered end section 42 typically make an angle of between about 5 degrees and about 30 degrees and is preferably between about 15 degrees and about 25 degrees with the axis of the obturator 14. Tip 20 also includes a second conically-tapered surface 48 that tapers from diameter 44 of obturator 14 to diameter 41 of obturator shaft 24. The surface of tapered section 48 typically makes an angle of between 10 degrees and about 50 degrees and is preferably between about 20 degrees and about 25 degrees. Obturator 14 may also include a land section 50 having a first leading tapered surface 52 and a second trailing tapered surface 54 and a diameter 56. Land section 50 helps to center obturator 14 within cannula tube 16 during insertion and removal of obturator 14. Tapered surfaces 52, 54 aid in facilitating the insertion and removal of obturator 14 through the seal(s) of the cannula head. Diameter 56 of land section 50 is typically greater than the diameter 41 of shaft 24 but less than maximum diameter 44. Land section 50 typically has a length 58 approximately equal to diameter 41 of shaft 24.

As shown in FIG. 10A, obturator 14 is inserted into cannula tube 16. According to the present invention, cannula tube 16 is circular in cross-section and has a relatively uniform inside diameter 60 and outside diameter 62 along almost the entire length of tube 16. Inside diameter 60 is typically greater than diameter 44 of obturator 14 to ensure that obturator 14 can be inserted without obstruction into cannula tube 16. However, according to one aspect of the present invention, cannula tube 16 includes an end 64 that is uniformly continuous and thus has no interruptions, such as slots, holes, or other apertures. Such a uniform, continuous geometry minimizes the resistance to insertion through and removal from tissue, minimizes the potential for tissue to be torn or damaged during insertion and removal, and also minimizes the potential for damage to sutures, other instruments, and the trocar itself during insertion or removal. Furthermore, according to this aspect of the present invention, internal diameter 60 and outside diameter 62 of cannula tube 16 decrease at end 64. As more clearly shown in the detailed view of FIG. 10B, at end 64 of tube 16, the inside diameter 60 and outside diameter 62 taper to a minimum diameter, for example, inside diameter 60 may decrease to a minimum diameter 66 and outside diameter 62 may decrease to minimum diameter 67. (In the detail shown in FIG. 10B, for clarity of illustration, diameters 44, 60, 62, 66, and 67 are shown as single-headed arrows. These single-headed arrows represent the respective double-headed arrows by which diameters are typically illustrated, for example, the double-headed arrow representing diameter 44 in FIG. 10A.) In one embodiment, diameters 66 and 67 may essentially be the same such that the cross-section of end 64 comes to a point. According to this aspect of the present invention, inside diameter 66 of end 64 of cannula tube 16 is smaller than diameter 44 of obturator 14.

According to this aspect of the invention, though the entire cannula tube 16 can be made of flexible material, at least end 64 of cannula tube 16 is typically made of a flexible material, for example, a thermoplastic polymer, such as a polycarbonate or its equivalents, or a thermoset polymer, such as a polyurethane or its equivalents. Therefore, when obturator 14 having a maximum diameter 44, greater than diameter 66, is inserted into the cannula tube 16 by means of, for example, the hole 119 (see FIG. 9), and as tip 20 of obturator 14 approaches end 64 of cannula tube 16, the surface 42 of tip 20 comes into contact with the inside diameter 66 of end 64. As tip 20 passes through end 64, surface 42 continues to pass through or bear against inside diameter 64 until the diameter of surface 42 approaches or exceeds diameter 66. Since end 64 is comprised of a flexible material, as diameter 44 of tip 20 approaches and bears against inside diameter 66, inside diameter 66 will radially deflect until the inside diameter reaches or exceeds diameter 44. After diameter 44 passes diameter 66, the flexible end 64 recovers, that is, elastically, though some incidental plastic deformation may occur, to essentially its original undeflected diameter, for example, a diameter less than diameter 44. In this aspect of the invention, after the diameter 44 passes inside diameter 66, inside diameter 66 of end 64 bears against the surface 48, as shown in FIG. 10B. In a preferred aspect, inside diameter 66 of flexible end 64 returns to a diameter wherein outside diameter 67 is less than diameter 44. The resulting assembled trocar 10 having cannula 16 and obturator 14 provides a relatively uniform transition between surface 42 of tip 20 and the outside surface of end 64 such that little or no resistance is provided and little or no damage occurs when subsequently inserting trocar 10 through tissue.

As is typical in the art, trocar 10 may be inserted through a patient's skin by first cutting a small incision in the skin. When tip 20 of obturator 14 has a pointed tip or a tip with cutting blades, skin incision may not be necessary. When trocar 10 penetrates the skin and underlying tissue and accesses the body cavity to be examined or treated, for example, the chest cavity, obturator 14 is removed from cannula 16. According to the present invention, the obturator 14 may be removed from trocar 10 by exerting an axial force on the cannula cap assembly, for example, cap assembly 22 (see FIG. 1) while manually restraining the cannula assembly, for example, by holding cannula assembly 12 by means of head assembly 18 of FIG. 1.

With reference to FIGS. 10A and 10B, as obturator 14 is withdrawn, tapered surface 48 of obturator 14 bears against the surface of inside diameter 66 of tip 64 and, again, diameter 66 is radially deflected. Again, diameter 66 of flexible end 64 continues to radially deflect (again, preferably elastically though some plastic deformation may occur) as obturator 14 is withdrawn until diameter 66 meets or exceeds diameter 44 of tip 20, after which the obturator can be removed typically without obstruction and the diameter 66 can flexibly return to a diameter that approaches or attains its original diameter. It will be understood by those of skill in the art that the diameter 66 may not return to its original diameter due to plastic deformation during insertion or removal of obturator 14. However, in one aspect of the invention, flexible cannula tube 16 may be removable and disposable such that re-use is not required. Similarly, according to one aspect of the invention, the cannula head assembly, for example, head assembly 118 may also be disposable or reusable.

However, according to one aspect of the invention, the axial force applied to the obturator 14 is provided by the rotation of the obturator 14 about its axis and the slidable engagement of one or more bearing surfaces on obturator cap assembly 22 and cannula head assembly 18 (see FIG. 1). That is, though the inventions disclosed in FIGS. 1, 2, 3, 4A through 4D, 5A though 5C, 6 through 9, and FIGS. 11A through 11D, and FIGS. 12A through 12D and the invention disclosed in FIGS. 10A and 10B may be practiced independently, these inventions may also be combined to provide a trocar assembly that provides the benefits of both inventions, that is, unobstructed ease of insertion into a body cavity and ease of removal of the obturator from tissue and from the cannula with minimal damage to tissue.

FIGS. 11A through 11D illustrate a further aspect of the present invention. FIG. 11A illustrates an obturator cap 722 attached to an obturator shaft 714 and a cannula head assembly 718 having a rotatable lever 750. Lever 750 is rotatably mounted to head assembly 718 by means of pin 751. The section view identified by reference numbers 11B—11B in FIG. 11A is shown in FIG. 11B. As shown in FIG. 11B, lever 750 includes a notch 752. A perspective view of lever 750 is shown in FIG. 11D which clearly shows notch 752 and pin 751. FIG. 11C illustrates the axial deflection of cap 722 and shaft 714 according to this aspect of the invention. As shown by arrow 760 in FIG. 11C, the desired axial deflection of shaft 714 is effected by pivotally rotating lever 750 about pin 751 whereby the surface of notch 752 bears against the bottom of cap 722 and axially deflects cap 722 and shaft 714. Though a single lever 750 is shown in these figures, one or more levers may be used. The shape of lever 750 and its means of attachment to head assembly 718 are not limited to those shown. The shape of lever 750 and its means of attachment may be modified as desired to effect the desired function. In addition, according to the present invention, lever 750 may be mounted to obturator cap 722, instead of to head assembly 718, and still effect the desired deflection.

FIGS. 12A through 12D illustrate a further aspect of the present invention. FIG. 12A illustrates an obturator cap 822 attached to an obturator shaft 814 and a cannula head assembly 818 having at least one moveable wedge 850. Obturator cap 822 includes at least one wedge-shaped recess 855, corresponding to wedge 850, having a complementary bearing surface 856 (shown most clearly in FIG. 12C). Wedge 850 is slidably mounted in a slot 853 (see FIG. 12C) in head assembly 818 by means of tab 851. Wedge 850 includes a bearing surface 852. The section view identified by reference numbers 12B—12B in FIG. 12A is shown in FIG. 12B. A perspective view of wedge 850 is shown in FIG. 12D which clearly shows bearing surface 852 and tab 851. As shown in FIG. 12B, wedge 850 is slidable, as indicated by arrow 860, in slot 853 from a first position to a second position, shown in phantom by reference number 850'. According to the present invention, the axial deflection of cap 822 is effected by sliding wedge 822 in the direction of arrow 860. FIG. 12C illustrates the axial deflection of cap 822 and shaft 814 according to this aspect of the invention. The desired axial deflection of shaft 814 is effected by sliding wedge 850 along slot 853 as shown by arrow 860 whereby the bearing surface 852 of wedge 850 bears against the corresponding surface 856 in recess 855 of cap 822 and axially deflects cap 822 and shaft 814. The shape of wedge 850 and its means of attachment to head assembly 818 are not limited to those shown. The shape of wedge 850 and its means of attachment may be modified as desired to effect the desired function. For example, the angle of inclination of surface 852 of wedge 850 may vary from about 5 to about 85 degrees, but is preferably between about 20 and about 50 degrees. In addition, according to the present invention, wedge 850 may be slidably mounted to obturator cap 822, instead of to head assembly 818, and the angled recess 855 may be located in head assembly 818, instead of in cap 822, and still effect the desired deflection.

A broad range of sizes of cannulas 12 (or 812, etc.) and obturators 14, (or 814, etc.) may be used for the present invention. However, cannula tube 16 is typically sized to accommodate standard surgical instruments that could be inserted into tube 16 to treat a patient. For example, conventional surgical instruments that may be used with the present invention typically have outside diameters ranging from about 3 mm to about 15 mm. Therefore, inside diameter 60 of cannula tube 16 may typically range from about 3 mm (0.118 inches) to about 15 mm (0.591 inches), and is preferably between about 5 mm (0.197 inches) and about 12 mm (0.472 inches). In order to operate according to the present invention, the maximum diameter 44 of obturator 14 is typically at least about 0.001 inches (0.025 mm) to about 0.020 inches (0.51 mm) greater than the inside diameter 66 of cannula 16, and is preferably between about 0.004 inches (0.102 mm) to about 0.007 inches (0.178 mm) greater than diameter 66. That is, the maximum diameter 44 of obturator 14 typically ranges from about 0.119 inches (3 mm) to about 0.611 inches (15.5 mm).

The inside diameter 60 of cannula 16 is typically slightly larger than the maximum diameter 44 of obturator 14 to allow obturator 14 to slide in and out of cannula tube 16 with little or no obstruction or resistance. Diameter 60 is typically between about 0.005 inches (0.127 mm) to about 0.050 inches (1.27 mm) larger than diameter 44, and is preferably between about 0.010 inches (0.254 mm) to about 0.020 inches (0.508 mm) greater than diameter 44. It will be apparent to those of skill in the art that diameter 60 may even be larger than diameter 44, for example, diameter 60 may be more than 0.050 inches larger than diameter 44. But the larger the clearance is between inside diameter 60 and outside diameter 44, the larger the outside diameter 62 of cannula tube 16 must be. However, the larger the diameter 62 is, the larger is the wound or penetration through the tissue of the patient. Of course, the size of this penetration through the tissue is preferably minimized and, correspondingly, the clearance between diameter 44 and diameter 62 is preferably minimized. Thus, the diameter 60 is typically between about 0.124 inches (3.15 mm) to about 0.661 inches (16.79 mm).

Again, the outside diameter 62 of cannula tube 16 is preferably minimized to minimize the size of the penetration through the tissue of the patient. However, the size of diameter 62 is dictated by, among other things, the inside diameter 60 and the thickness of the tube 16 required to manufacture tube 16 (typically made of plastic), for example, to supply the desired rigidity. Accordingly, the outside diameter 62 of tube 16 typically ranges from about 0.165 inches (4 mm) to about 0.761 inches (19.3 mm) and is preferably between about 0.365 inches (9.3 mm) and about 0.577 inches (14.6 mm).

Figure 13:
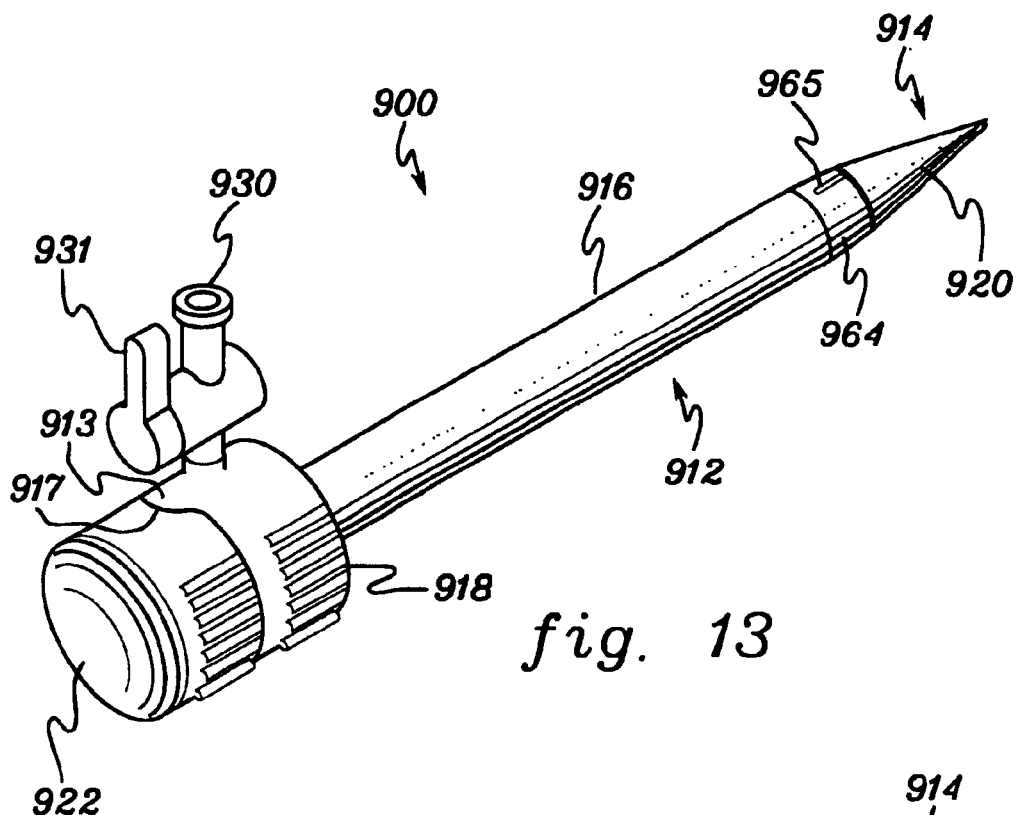
FIG. 13 illustrates a perspective view of a trocar embodying aspects of the present invention.

FIGS. 13 through 16 illustrate further aspects of the present invention. The trocar 900 illustrated in these figures is marketed under the name TroGard® Finesse™ by the ConMed Corporation of Utica, N.Y. FIG. 13 illustrates a perspective view of trocar 900 having a cannula assembly 912 including a cannula head assembly 918 and a cannula tube 916 and an obturator 914 having a pointed tip 920, a cap assembly 922, and a shaft 924 (shown in FIG. 15) between pointed tip 920 and cap assembly 922. The cannula tube 916 includes an opened end 964. Cannula head assembly 918 may include one or more gas supply or removal ports 930 having a valve 931, which operate and function in the essentially the same fashion as port 130 and valve 131 shown in FIGS. 9 and 10. The use and operation of trocar 900 is essentially the same as trocar 10 shown in FIGS. 1, 2 and 3.

According to this aspect of the present invention, cannula head assembly 918 includes at least one recess 917, typically at least two evenly-spaced recesses 917, and obturator cap assembly 922 include at least one projection 913, typically at least two evenly-spaced projections 913. Recesses 917 and projections 913 cooperate to effect the desired deflection of obturator 914 relative to cannula assembly 912. For example, in a fashion essentially identical to that discussed with respect to earlier aspects of the invention, after insertion of trocar 900 into a body cavity, obturator 914 is at least partially removed from the body cavity by rotating the obturator 914 relative to cannula assembly 912. This is more clearly shown in FIG. 14.

Figure 14:
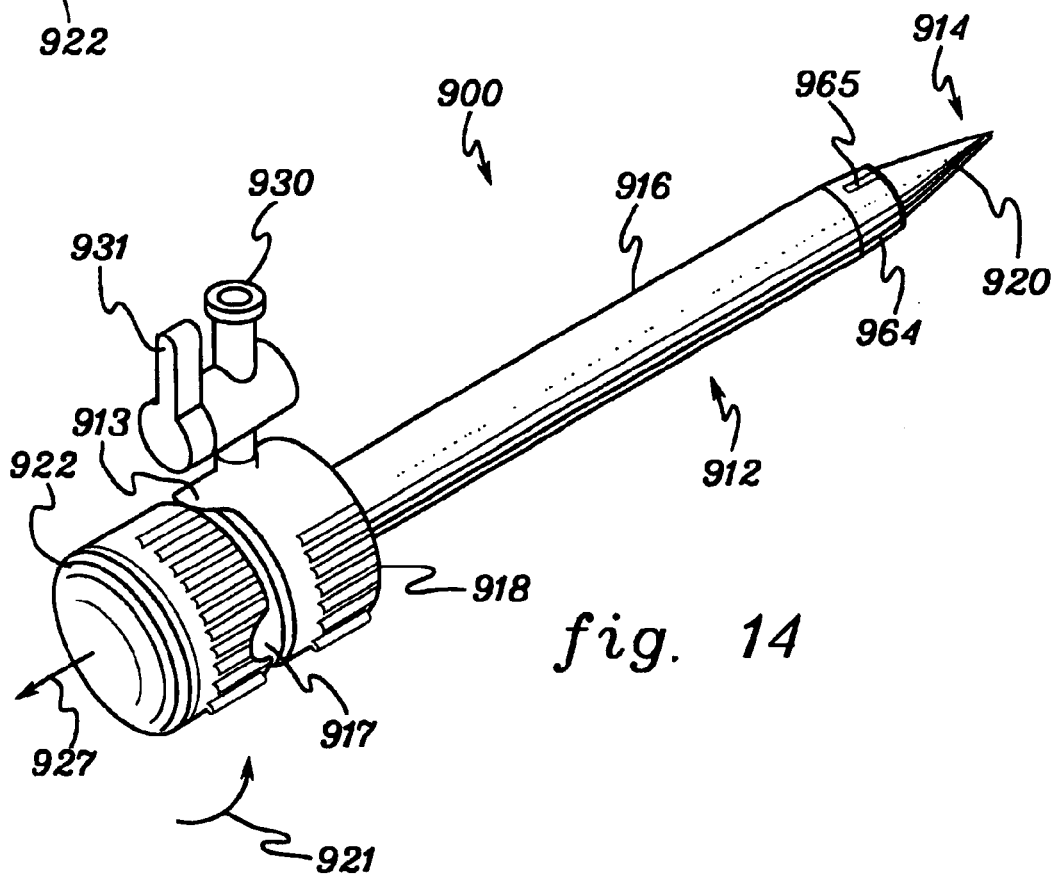
FIG. 14 is a perspective view illustrating the operation of the device shown in FIG. 13.

FIG. 14 is a perspective view of trocar 900 that is similar to FIG. 13 but illustrating the typical position of obturator 914 relative to cannula assembly 912 after rotation and deflection of obturator 914. The rotation of obturator 914 is generally illustrated by the curved arrow 921 and the resulting axial deflection of obturator 914 relative to cannula assembly 912 is generally illustrated by arrow 927. Again, as before, the rotation of obturator 914 causes the surface of recesses 917 to bear against and "ride-up" on projections 913 whereby obturator 914 is axially deflected relative to cannula assembly 912. In the aspect of the invention shown in FIGS. 13 and 14, projections 913 and recesses 917 are generally elliptical in shape, though, as discussed above, other shapes or contours may be used.

As shown in FIG. 14, the deflection of cap assembly 922 also deflects obturator tip 920 to effect at least partial removal of obturator 914 from the body cavity. Open end 964 of cannula tube 916 and obturator tip 920 may include the geometry and geometrical relationship illustrated in FIGS. 10A and 10B, that is, the geometry of tip 920 may radially deflect open end 964 as obturator 914 is axially deflected while providing a smooth and continuous outer surface. However, though in one aspect of the invention, the outer surface of open end 964 is smooth and continuous, having no obstructions, dislocations, or slots, according to the aspect of the invention shown in FIGS. 13 and 14, open end 964 may also include one or more axial slots 965, to more readily allow open end 964 to radial deflect when impinged upon by the surfaces of tip 920. (This impingement and deflection are again clearly shown in FIGS. 10A and 10B.)

FIGS. 15 and 16 illustrate cross-sectional views of trocar 900 shown in FIGS. 13 and 14, respectively. For illustrative purposes, port 930, valve 931, and obturator shaft 924 are not shown in cross section in FIGS. 15 and 16. As shown in FIG. 15, when obturator 914 is inserted into cannula assembly 912 prior to insertion into a body cavity by a surgeon, the outer surface of open end 964 of cannula tube 916 and the outer surface of tip 920 of obturator 914 provide a relatively smooth profile which minimizes the insertion effort required by the surgeon and minimizes the potential for damaging skin, tissues, and internal organs during insertion, that is, there are no projecting edges upon which tissue can be damaged. As shown in FIG. 16, during and after obturator 914 is axially deflected, the cooperating geometry of open end 964 and tip 920 radially deflect open end 964 so that tip 920 can readily pass the restriction provided by open end 964 and allow for easy removal of obturator 914 by the surgeon.

FIGS. 15 and 16 also illustrate the seal element 970 located in cannula head assembly 918. Sealing element 970 is typically made from a resilient or elastomeric material, for example, silicone rubber, polyurethane elastomer, neoprene or thermo plastic elastomer. Sealing element 970 allows for the easy insertion and removal of obturator shaft 924 into cannula assembly 912 while minimizing the release of fluids, that is, liquids or gases, from the cannula assembly 912. Sealing element 970 is more completely illustrated and described with respect to FIGS. 17, 18A, 18B, and 18C.

Figure 17:
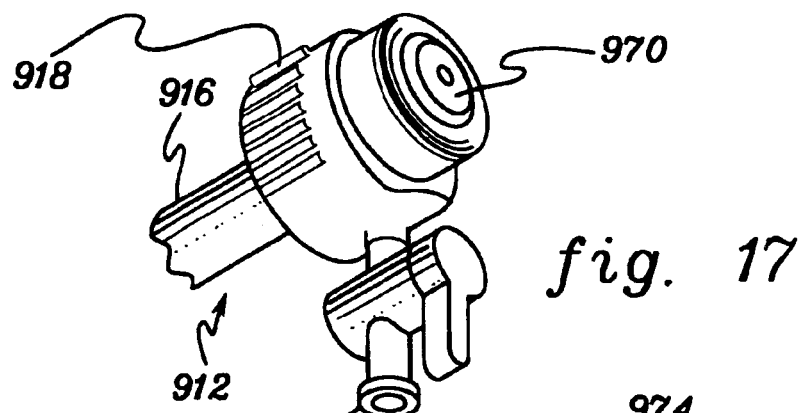
FIG. 17 is a partial perspective view of the cannula head assembly shown in FIGS. 13 through 16.

FIG. 17 illustrates a perspective view of the end of cannula assembly 912 having head assembly 918 and tube 916. Sealing element 970 is positioned in cannula head 918.

Figure 18A:
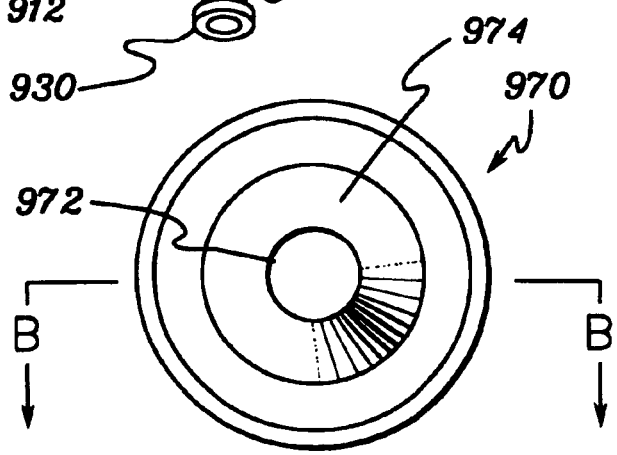
FIGS. 18A through 18C are a top view, cross-sectional view, and bottom view, respectively, of the seal element shown in FIG. 17.
Figure 18B:
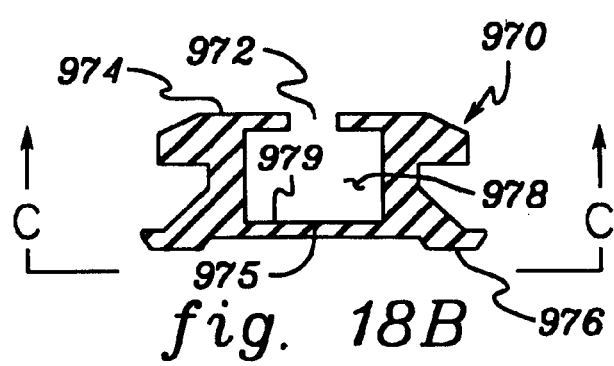
Figure 18C:
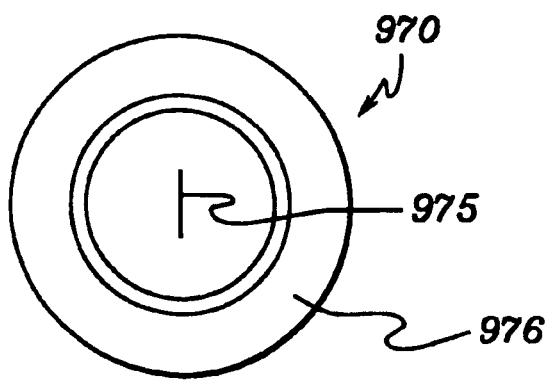

FIGS. 18A, 18B, and 18C illustrate a top view, cross-sectional view, and bottom view, respectively, of sealing element 970. As shown in FIG. 18A, sealing element 970 is circular in shape and includes a centrally located aperture or hole 972, though which the obturator shaft 924 is inserted and removed, and a top surface 974. Sectional view B—B identified in FIG. 18A is shown in FIG. 18B. As shown in FIG. 18B, sealing element 970 includes a bottom surface 976 and an internal cavity 978. Bottom surface 976 comprises a membrane 979 which includes at least one aperture 975, for example, one or more narrow slits, though other shaped apertures may be used. The length of aperture 975 is designed to allow passage of obturator shaft 924 while minimizing leakage of fluids. The thickness of membrane 979 is typically designed to withstand the differential pressure across it which minimizes the passage of fluid through aperture 975. If two or more narrow slits are used in membrane 979, the slits are preferably radially directed and equally spaced in membrane 979. The profile of the outside diameter of sealing element 970 is adapted to be inserted and retained within head assembly 918. As shown in FIGS. 15 and 16, sealing element 970 may be sized to be inserted and retained within head assembly 918 by simple interference fit. However, sealing element 970 may also be retained by appropriate fasteners or retaining elements, such as by means of a plastic or metallic seal-retaining ring. Bottom view C—C identified in FIG. 18B is shown in FIG. 18C. The relative length of aperture 974 is shown in FIG. 18C.

When inserting obturator 914 into cannula assembly 912, tip 920 is inserted into and through aperture 972 and then through aperture 974. The aperture 972 is sized so that its diameter is slightly smaller than the smallest diameter of obturator shaft 924 or the smallest diameter surgical instrument to be used. For example, the diameter of aperture 972 is slightly smaller than diameter 41 in FIG. 10A. This interference fit between the resilient diameter of aperture 972 and shaft 924 minimizes the passage of fluids from cavity 978 to the ambient environment during insertion and removal of obturator 914. As the tip 920 of obturator 914 passes through aperture 974, the narrow width of aperture 974, typically simply a slit in membrane 979, provides a sealing means. This sealing means minimizes the passage of fluids from within cannula head 918 to sealing element cavity 978, and also to the ambient environment. This prevention or minimization of fluid passage is essentially maintained while the obturator 914 is inserted, retained in, and removed from cannula assembly 912. When obturator 914 is removed from cannula assembly 912 and shaft 924 is removed from apertures 972 and 975, the mating surfaces of aperture 974 provide a sealing means which minimizes the passage of fluids from cannula head 918 to the ambient environment.

It will be understood by those of skill in the art that the diameter and thickness of sealing element 970, the size of apertures 972 and 974, and the thickness of membrane 979 may vary and depending upon the size of cannula head 918, the size of obturator 914, and the difference in pressure across membrane 979 that needs to be sealed, among other things. However, in the aspect of the invention shown in FIGS. 18A–1BC, the outside diameter of sealing element 970 is between about 0.625 inches and about 0.75 inches; the thickness of sealing element 970 is between about 0.25 inches to about 0.50 inches; the diameter of aperture 972 is about 0.0625 inches to about 0.1875 inches; the length of aperture 974 is between 0.1875 inches to about 0.25 inches; and the thickness of membrane 979 is between about 1 mm to about 3 mm.

Figure 19C:
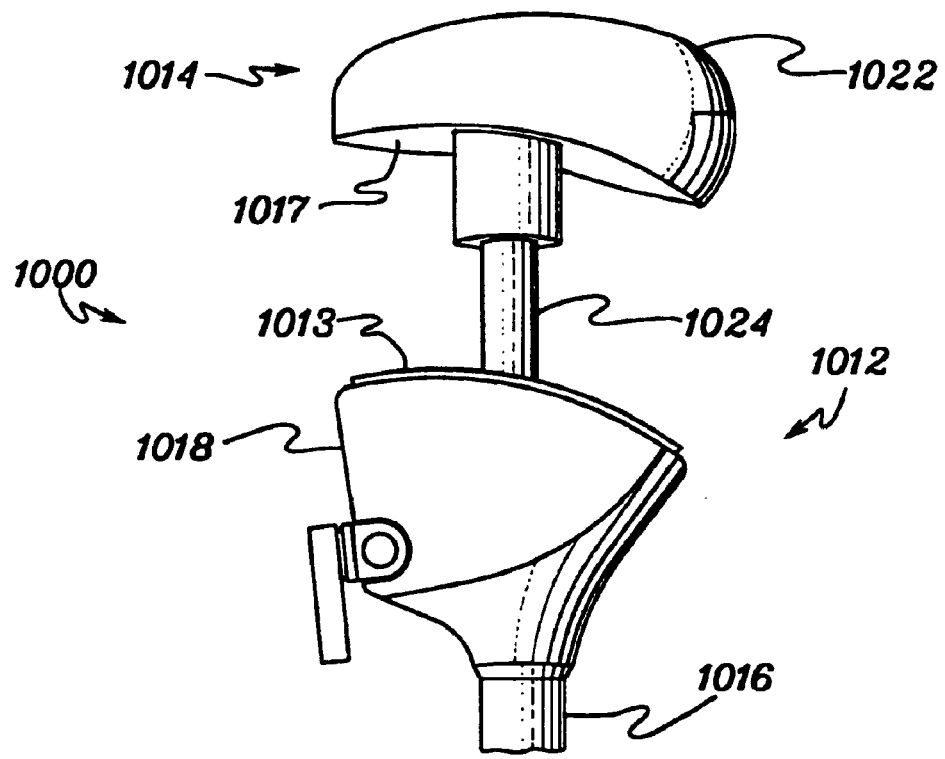

A further aspect of the present invention is illustrated in FIGS. 19A through 19E. FIGS. 19A through 19C are a side view, top view, and perspective view, respectively, of a trocar 1000 according this aspect of the invention. FIG. 19A illustrates a side elevation view of trocar 1000 having a cannula assembly 1012 including a cannula head assembly 1018 and a cannula tube 1016 and an obturator 1014 including a cap assembly 1022, and a shaft 1024 (See FIG. 19C.). Cannula head assembly 1018 may include one or more gas supply or removal ports 1030 having a valve 1031, which operate and function in the essentially the same fashion as port 130 and valve 131 shown in FIGS. 9 and 10. The use and operation of trocar 1000 is essentially the same as trocar 10 shown in FIGS. 1, 2 and 3, except as described below. Though not shown in FIG. 19A, in one aspect of the invention, cannula head 1018 includes a sealing element similar to sealing element 970 shown in FIGS. 18A through 18C. Cannula tube 1016 and obturator 1014 may include the similar geometry and geometrical relationship illustrated in FIGS. 10A and 10B.

FIG. 19B illustrates a top view of trocar 1000 shown in FIG. 19A. As shown, according to this aspect of the invention obturator cap 1022 is oval or egg-shaped. (Note that cannula head 1018 will also have a comparable shape.) This shape not only provides a convenient shape that facilitates handling and rotation of obturator cap 1022 by the surgeon, but the shape shown in FIG. 19B also provides a corresponding bearing surface contour that effects the desired deflection when rotated. The shape of obturator cap 1022 (and cannula head 1018) may also have other shapes, for example, circular, rectangular, square, and triangular, among others, and still effect the desired invention, though these shapes may not be as easily to manipulated by the surgeon.

According to this aspect of the present invention, the deflection of obturator 1014 relative to cannula head assembly 1018 is effected by rotating obturator cap 1022 relative to cannula head assembly 1018 as indicated by arrow 1021 whereby the bottom surface 1017 of obturator cap 1022 bears against the top surface 1013 of head assembly 1018. That is, unlike earlier aspects of the invention in which a recess or projection provided one or more bearing surfaces, in this aspect of the invention, the entire bottom surface 1017 of obturator cap 1022, and any portion thereof, and the entire top surface 1013 of head assembly 1018, and any portion thereof, may act as a bearing surface to cause the deflection of obturator 1014 relative to cannula 1012. It will be understood by those of skill in the art that only a portion of surface 1017 or surface 1013 may provide a bearing surface and the entire surfaces 1017 and 1013 may not be impinged upon. For example, while the cannula assembly 1012 is held by the surgeon and the obturator 1014 is twisted, as the obturator 1014 rotates, the point of impingement of the upper surface 1017 upon the lower surface 1013 will typically vary with rotation as the upper surface 1017 "rides up on" the lower surface 1013. This impingement and deflection are more clearly illustrated in FIG. 19D. Though the surfaces 1017 and 1013 in FIG. 19A are shown as being generally curvilinear in shape, these surfaces may also be linear or planar and still effect the desired deflection upon rotation (for example, as shown in FIG. 19E).

FIG. 19C illustrates a perspective view of trocar 1000 shown in FIGS. 19A and 19B. This perspective view is taken from a position slightly below the horizontal to better illustrate the shape of the features of this aspect of the invention. In FIG. 19 shows obturator 1014 somewhat withdrawn from cannula 1012 to facilitate illustration of the geometry of obturator cap 1022 and cannular head assembly 1018. As shown, bearing surface 1017 of obturator cap 1022 is a curved surface. When obturator 1014 is inserted in cannula 1012, bearing surface 1017 abuts surface 1013 of cannula head assembly 1018. Though not shown in FIG. 19C, the surface 1013 of cannula head assembly 1018 has a shape similar to surface 1017. Obturator shaft 1024 is also shown in FIG. 19C. The rotation and deflection of obturator 1014 relative to cannula 1012 is illustrated in FIG. 19D.

Figure 19D:
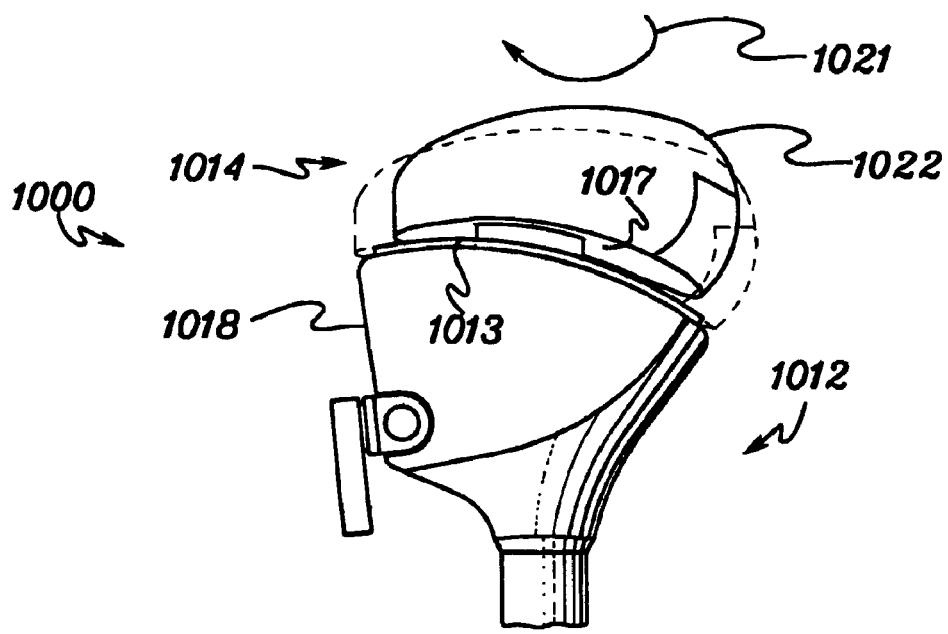
FIG. 19D is side view of the aspect of the invention shown in FIGS. 19A through 19C illustrating the operation of this aspect of the invention.

FIG. 19D illustrates a perspective view of trocar 1000 shown in FIGS. 19A, 19B, and 19C. The unrotated obturator cap 1022 is shown in phantom to illustrate the relative rotation and deflection of obturator 1014 relative to cannula 1012. The relative rotation of obturator 1014 is indicated by curved arrow 1021. Due to the geometry of mating surface 1013 and 1017, as obturator 1014 is rotated, typically manually by a surgeon while the surgeon holds cannula 1012 stationary, at least some portion of surface 1017 bears against and "rides up" on surface 1013 lifting or displacing obturator 1014 relative to cannula 1012. A rotation as small as 5 degrees will result in a relative deflection of obturator 1014; however, obturator 1014 will typically be rotated at least 15 degrees, preferably at least 90 degrees, to effect the desired deflection. As noted previously, this axial deflection of obturator 1014 typically at least partially dislodges the tip of the obturator shaft (see tip 920 in FIGS. 15 and 16, for example) from the body cavity in which trocar 1000 is inserted. As noted with respect to FIGS. 19A through 19C, the deflection effected by rotating obturator 1014 may also be sufficient to deflect the end of shaft 1024 beyond the flexible restriction at the end of cannula tube 1016, for example, as shown in FIGS. 10A and 10B.

FIG. 19E illustrates a side elevation view similar to FIG. 19A of another trocar 1100 according to another aspect of the present invention. In this aspect, trocar 1100 includes a obturator cap 1122 having a bearing surface 1117 and a cannular head 1118 having a bearing surface 1113 which mates with surface 1117. In contrast to the embodiment shown in FIGS. 19A through 19D, surfaces 1113 and 1117 are linear, or non-curved, yet can still effect the desired axial deflection when obturator cap 1112 is rotated relative to cannula head 1118.

While the invention has been particularly shown and described with reference to preferred embodiment, it will be understood by those skilled in the art that various changes in form and details may be made to the invention without departing from the spirit and scope of the invention described in the following claims.

What is claimed is:

1. A trocar comprising:
   an elongated cannula member having a first camming surface formed on a proximal end thereof and a radially-expandable opening formed on a distal end thereof;
   an elongated obturator adapted to be inserted into the cannula for rotational and axial movement therein, said obturator comprising a shaft having a distal end;
   a point formed on the distal end of the shaft, said point tapering distally from a maximum diameter band and tapering proximally from said band to the shaft, said band being larger in girth than the distal cannula opening;
   said band being distally adjacent the distal cannula opening when the obturator is substantially fully inserted into the cannula; and
   a cap formed on a proximal end of the obturator, said cap having a second camming surface positioned thereon for engagement with the first camming surface when the obturator is substantially fully inserted into the cannula,
   said first and second camming surfaces being effective to cause proximal axial displacement of the obturator with respect to the cannula member when the cap is rotated with respect to the cannula member, said distal cannula opening expanding radially as the maximum diameter band moves proximally through it; and
   wherein said radially-expandable opening at the first end of the cannula member comprises a smooth and continuous circumferential wall.

2. The trocar as recited in claim 1, wherein the cannula further comprises a head assembly formed on the proximal end thereof, and the head assembly comprises a seal which permits the passage of the obturator through the head assembly with little or no fluid leakage.

3. The trocar as recited in claim 2, wherein the head assembly further comprises a fluid port.

4. The trocar as recited in claim 3, wherein the fluid port includes a valve.

5. The trocar as recited in claim 1, wherein the first camming surface formed on the proximal end of the cannula comprises a surface of a projection on a periphery of a head assembly positioned on the proximal end of the cannula and the at least one second bearing surface comprises a surface of a recess positioned on a periphery of the cap assembly of the obturator.

6. The trocar as recited in claim 5, wherein the projection on the periphery of the head assembly comprises an elliptical projection and the recess on the periphery of the cap comprises an elliptical recess.

7. The trocar as recited in claim 1, wherein at least one of the first camming surface and the second camming surface comprises an inclined surface.

8. The trocar as recited in claim 1, wherein at least one of the first camming surface and the second camming surface comprises one of a projection, a recess, and a boss.

9. The trocar as recited in claim 1, wherein at least one of the first camming surface and the second camming surface comprises one of a linear and a curvilinear surface.

10. The trocar as recited in claim 1, wherein the first camming surface comprises a first bearing surface and the second camming surface comprises a second bearing surface.

11. The trocar as recited in claim 1, wherein the first camming surface on the cannula is moveable relative to the cannula.

12. The trocar as recited in claim 1, wherein the second camming surface on the cap of the obturator is moveable relative to the obturator.

13. The trocar as recited in claim 1, wherein at least one of the cannula and the obturator is non-metallic.

* * * * *